United States Patent
Ito et al.

(10) Patent No.: US 10,022,056 B2
(45) Date of Patent: Jul. 17, 2018

(54) BLOOD PRESSURE MEASUREMENT CUFF AND ATTACHMENT METHOD FOR THE SAME

(71) Applicant: OMRON HEALTHCARE CO., LTD., Muko-shi, Kyoto (JP)

(72) Inventors: Shinichi Ito, Kyoto (JP); Tameo Ashida, Kyoto (JP); Masaki Harada, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 267 days.

(21) Appl. No.: 14/819,149

(22) Filed: Aug. 5, 2015

(65) Prior Publication Data

US 2016/0000342 A1 Jan. 7, 2016

Related U.S. Application Data

(63) Continuation of application No. PCT/JP2014/055488, filed on Mar. 4, 2014.

(30) Foreign Application Priority Data

Mar. 5, 2013 (JP) .................................. 2013-042843

(51) Int. Cl.
*A61B 5/00* (2006.01)
*A61B 5/022* (2006.01)

(52) U.S. Cl.
CPC .......... *A61B 5/02233* (2013.01); *A61B 5/022* (2013.01); *A61B 5/6824* (2013.01); *A61B 2560/04* (2013.01)

(58) Field of Classification Search
CPC ....... A61B 5/02; A61B 5/02233; A61B 5/022; A61B 5/6824; A61B 17/1322;

(Continued)

(56) References Cited

U.S. PATENT DOCUMENTS 869,030 A * 10/1907 Stenzy ................... A44B 11/04
                                                                           126/25 B
3,633,567 A * 1/1972 Sarnoff .............. A61B 5/02141
                                                                             600/499

(Continued)

FOREIGN PATENT DOCUMENTS

JP     H0515283 Y2     4/1993
JP     H05115447 A     5/1993

(Continued)

OTHER PUBLICATIONS

May 27, 2014 International Search Report issued in International Application No. PCT/JP2014/055488.

*Primary Examiner* — Patricia Mallari
*Assistant Examiner* — Sarah Kingsley
(74) *Attorney, Agent, or Firm* — Oliff PLC

(57) ABSTRACT

A blood pressure measurement cuff wrapped a direction along circumferential direction around a measurement site, the blood pressure measurement cuff containing fluid bladder between belt-shaped body composed of inner cloth to be in contact with the measurement site and outer cloth opposing the inner cloth. Ring attachment member attached to a region on inner circumferential end-side of the outer cloth and hook-and-loop fastener provided in a region on outer circumferential end-side of the inner cloth are included. The ring has a temporary fastening structure that allows a region continuous with outer circumferential end of the belt-shaped body to be pulled through ring with arm strength in a direction away from measurement site during attachment and suppresses a case in which the region continuous with the outer circumferential end of the belt-shaped body pulled by the arm strength is pulled back through the ring by elastic force of the measurement site.

12 Claims, 11 Drawing Sheets

(58) Field of Classification Search
CPC . A61B 17/135; A61B 17/132; A61B 17/1355; A61B 17/1325; A44C 5/2071; Y10T 24/4047; Y10T 24/4086; Y10T 24/4088; Y10T 24/4093; Y10T 24/4736; Y10T 24/4745; Y10T 24/4764
USPC .......................................... 224/166; 368/282
See application file for complete search history.

(56) References Cited

U.S. PATENT DOCUMENTS

| | | | | |
|---|---|---|---|---|
| 3,669,096 A | * | 6/1972 | Hurwitz | A61B 5/02233 600/499 |
| 4,832,040 A | * | 5/1989 | Ruff | A61B 5/02233 600/499 |
| 2010/0268100 A1 | * | 10/2010 | Nakanishi | A61B 5/02233 600/499 |

FOREIGN PATENT DOCUMENTS

| | | |
|---|---|---|
| JP | H08215159 A | 8/1996 |
| JP | 2011177429 A | 9/2011 |

\* cited by examiner

BLOOD PRESSURE MEASUREMENT CUFF AND ATTACHMENT METHOD FOR THE SAME

TECHNICAL FIELD

The present invention relates to a blood pressure measurement cuff, and more specifically relates to a cuff that is wrapped around and compresses a measurement site such as a measurement subject's arm or wrist for blood pressure measurement.

Also, the present invention relates to a blood pressure measurement cuff attachment method for attaching such a blood pressure measurement cuff to a measurement site.

BACKGROUND ART

Conventionally, as an example of this type of blood pressure measurement cuff, there is known to be a fold-back type of blood pressure measurement cuff (armband), such as that disclosed in Patent Document 1 (JP H08-215159A). As shown in FIG. 13(A), a cuff 100 includes an oval-shaped fold-back fitting 106 near one end 104e in a length direction of an outer cloth (surface cloth) 104 of the cuff 100, and includes a hook-and-loop fastener (engagement portion) 103 near another end (leading end) 104f in the length direction of the outer cloth 104. An air bladder 102 (see FIG. 12(D)) is contained between the outer cloth 104 and an inner cloth (underside cloth) 105 of the cuff 100. Also, in this example, a microphone 101 for observing a pulse sound is included at a portion approximately in the center in the length direction.

During attachment, as shown in FIG. 13(A), the cuff 100 is first made cylindrical by passing a leading end portion 104f through the ring-shaped fold-back fitting 106 with the outer cloth 104 of the cuff facing outward. Next, a left arm 90 serving as a measurement site is passed through the cylindrical cuff from a side at which the cylindrical cuff appears to the measurement subject to be in the form of a clockwise spiral (note that FIGS. 13(A) and (B) illustrate cross-sectional views of the left arm 90 as viewed from the measurement subject), and the left arm 90 is adjusted so that the microphone 101 is located almost on the central line of the arm when the palm of the hand has been turned upward. Next, the leading end portion 104f is pulled leftward as indicated by arrow A1 so that a gap between the inner cloth 105 of the cuff and the left arm 90 is mostly eliminated. Thereafter, as shown in FIG. 13(B), a portion continuous with the leading end portion 104f of the cuff is folded back as indicated by arrow B1 from the position of the fold-back fitting 106 and the hook-and-loop fastener 103 is fixed to an opposing portion 104x on the outer cloth 104. Thus, the cuff 100 is attached to the left arm 90 serving as the measurement site. Note that arrow A2 in FIG. 13(A) and arrow B2 in FIG. 13(B) each show tensile force received by the cuff.

In this state, air is pumped into or discharged from the air bladder 102 through an air tube using a pump, and based on the pulse sound observed using the microphone 101, the blood pressure is measured (Korotkoff method). Note that instead of using the Korotkoff method, the blood pressure can be measured using the oscillometric method (the cuff itself detects change in a pulsewave as a pressure sensor) as well.

CITATION LIST

Patent Literature

Patent Document 1: JP H08-215159A

SUMMARY OF INVENTION

Technical Problem

However, when the measurement subject, for example, attaches the cuff 100 to his or her own left arm 90, he or she positions his or her right hand leftward of the left arm 90 (i.e., lateral to the body) so as to pull the leading end 104f of the cuff 100 leftward (i.e., more laterally from the lateral side of the body) with the right hand as indicated by arrow A1 in FIG. 13(A), and is forced to perform an unnatural operation of folding back toward the right as indicated by arrow B1 in FIG. 13(B) while mostly maintaining the amount of tensile force so that the cuff 100 does not loosen. For this reason, the fold-back type of cuff is problematic in that the measurement subject needs a bit of skill to attach it by himself or herself.

In view of this, it is an object of the present invention to provide a blood pressure measurement cuff that a measurement subject can easily attach by himself or herself.

Also, it is an object of the present invention to provide a blood pressure measurement cuff attachment method according to which a measurement subject can easily attach such a cuff to a measurement site by himself or herself.

Solution to Problem

In order to resolve the foregoing problems, the blood pressure measurement cuff of the present invention is a blood pressure measurement cuff to be wrapped in one direction along a circumferential direction around a measurement site, the blood pressure measurement cuff including:

a belt-shaped body obtained by enveloping a fluid bladder with an inner cloth to be in contact with the measurement site and an outer cloth opposing the inner cloth;

a ring attached via a ring attachment member to a region on an inner circumferential end side of the outer cloth; and a hook-and-loop fastener provided in a region on an outer circumferential end side of the inner cloth and configured to be fixed detachably to the outer cloth, wherein the ring includes a first side that extends in a direction intersecting the circumferential direction, a second side that extends along the first side, and a pair of connecting portions that connect the ends of the first and second sides, and at least a portion of the first side is attached to a region on the inner circumferential end side of the outer cloth via the ring attachment member, and the ring has a temporary fastening structure that allows a region continuous with the outer circumferential end of the belt-shaped body to be pulled through the ring with arm strength away from the measurement site during attachment and suppresses a case in which a region continuous with the outer circumferential end of the belt-shaped body pulled by the arm strength is pulled back through the ring by elastic force of the measurement site.

In the present specification, "measurement site" refers to a site that can be wrapped by a cuff, such as an upper arm or a wrist, in order to measure a measurement subject's blood pressure.

"Wrapping in one direction along the circumferential direction" around the measurement site means wrapping the cuff (belt-shaped body) in the circumferential direction around the measurement site such that it overlaps itself without being folded back. In other words, it means that in a cross-sectional view along the length direction of the measurement site, the cuff (belt-shaped body) is wrapped around the measurement site in a spiral shape.

The belt-shaped body "containing a fluid bladder" means that a substantial portion of a fluid bladder, or in other words, a fluid chamber, is contained in the belt-shaped body. This does not necessarily mean that the entire fluid bladder is completely surrounded by the belt-shaped body. For example, a portion existing on the peripheral edge of the fluid bladder outside of the fluid chamber may be exposed to the outside of the belt-shaped body.

Also, "inner cloth" and "outer cloth" may each be composed of one layer or multiple layers of resin instead of merely being composed of cloths.

"Inner circumferential end" indicates an end on the side that is to be inward when the cuff (belt-shaped body) is wrapped in one direction (spiral shape in cross-sectional view) along the circumferential direction around the measurement site.

"Outer circumferential end" indicates the end on the side that is to be outward when the cuff (belt-shaped body) is wrapped in one direction (spiral shape in cross-sectional view) along the circumferential direction around the measurement site.

The blood pressure measurement cuff of the present invention is attached to a measurement site (a cuff for wrapping around a left arm is used for convenience in the description) as follows, for example. First, with the outer cloth of the belt-shaped body on the outer side, the measurement subject passes the outer circumferential end of the belt-shaped body through the ring attached to the region on the inner circumferential end side of the outer cloth, so as to make the belt-shaped body into a cylinder that is sufficiently wider than the left arm. Note that at this stage, the region in which the hook-and-loop fastener is provided on the inner cloth of the belt-shaped body is passed through the ring. Next, from the side at which the cylindrical belt-shaped body appears to the measurement subject to be in the form of a counterclockwise spiral (counterclockwise from the inner circumferential end to the outer circumferential end), the left arm is passed through the cylindrical belt-shaped body. Then, adjustment is performed so that the ring is located below the measurement site. Next, the measurement subject temporarily pulls the outer circumferential end of the belt-shaped body downward with the right hand so as to substantially eliminate a gap between the inner cloth of the belt-shaped body and the left arm (this operation will be referred to as "temporary fastening" as appropriate). At this time, the ring allows the region continuous with the outer circumferential end of the belt-shaped body to be pulled downward (in a direction away from the measurement site) through the ring by the arm strength of the right hand. Meanwhile, the temporary fastening structure of the ring suppresses a case in which the region continuous with the outer circumferential end of the belt-shaped body pulled by the arm strength is pulled back through the ring by the elastic force of the measurement site. Accordingly, even if the measurement subject reduces the force with which the right hand pulls, a case in which the belt-shaped body loosens is suppressed. Thereafter, the measurement subject uses the right hand (e.g., moves the right hand upward on the torso side of the left arm) to, along the circumferential direction of the left arm, align the region continuous with the outer circumferential end of the belt-shaped body with a portion that has not passed through the ring of the belt-shaped body. Accordingly, the hook-and-loop fastener provided in the region on the outer circumferential end side of the inner cloth is fixed to the opposing portion of the outer cloth (this operation will be referred to as "actual fixing" as appropriate). Thus, the cuff is attached in one direction along the circumferential direction to the left arm serving as the measurement site. That is to say, when viewed by the measurement subject along the length direction of the measurement site, it is attached in a counterclockwise spiral shape.

Note that if the right arm is to be used as the measurement site, it is sufficient that a cuff with a left-right inverted structure is created and the above description of the method for attachment to the left arm is read replacing "left" with "right". Also, if a wrist or the like is to be used as the measurement site, it is sufficient that "upper arm" is replaced with "wrist" or the like (the same follows in the following description).

Thus, the blood pressure measurement cuff does not require an unnatural operation during attachment, unlike the case of the fold-back type of cuff described above. In particular, during the above-described temporary fastening to the left arm, the measurement subject need only temporarily pull the outer circumferential end of the belt-shaped body downward with the right hand. The operation for temporary fastening is not an operation in which the hand moves further laterally from the lateral side of the body, and there is no need for the measurement subject to continue to use his or her arm strength to maintain the tensile force of the belt-shaped body until the actual fixing is complete. Accordingly, the measurement subject can easily attach the blood pressure measurement cuff by himself or herself. For example, an elderly person with little flexibility or a sick person with little arm strength can perform attachment easily by himself or herself.

Also, in the state of being attached after the actual fixing is complete, the blood pressure measurement cuff is wrapped in one direction along the circumferential direction around the measurement site. That is to say, in the entire region along the circumferential direction of the measurement site, the inner cloth is hidden, and only the outer cloth can be seen on the outside. Usually, in order to compress the measurement site, the inner cloth is set to have a large amount of elasticity, and the outer cloth is set such that it has less elasticity than the inner cloth (or is not elastic). In this case, when air is pumped into the fluid bladder with a pump for blood pressure measurement, with the blood pressure measurement cuff, the cloth seen on the outside (outer cloth) does not needlessly inflate outward (to the side opposite to the measurement site). Accordingly, the amount of air supplied to the fluid bladder can be suppressed, resulting in an increase in the efficiency of pressurization.

Also, with the blood pressure measurement cuff, since the cloth seen on the outside (outer cloth) cannot inflate outward, the measurement subject is not caused to feel uneasy.

Furthermore, with the blood pressure measurement cuff, since the cloth seen on the outside (outer cloth) never needlessly swells outward, an arrangement is possible in which the fluid bladder is extended over most of the region in the circumferential direction (length direction) in the belt-shaped body. With this kind of arrangement, there is no longer a restriction (described below) on the extension range of the air bladder in the circumferential direction in the case of the fold-back type of cuff, and thus the range of dimensions in the circumferential direction of the measurement site set as specifications of the cuff (refers to a range ranging from the minimum circumference to the maximum circumference. The same follows below.) can be widened.

Also, it is known that the compression force compressing the artery of the measurement site depends on the dimension in the circumferential direction of the fluid bladder and the dimension in the width direction that intersects the circumferential direction. The larger the dimension in the circumferential direction and the dimension in the width direction of the fluid bladder are, the larger the compression force is. Here, according to the arrangement in which the fluid bladder is extended over most of the region in the circumferential direction, the dimension in the width direction of the fluid bladder can be reduced instead in order to obtain the needed compression force. If the dimension in the width direction of the fluid bladder is thus reduced, and the dimension in the width direction of the belt-shaped body is accordingly reduced, the measurement subject can more easily attach the blood pressure measurement cuff. Also, if the dimensions in the width direction of the fluid bladder and the belt-shaped body are reduced, the cost of materials can be reduced. Accordingly, the blood pressure measurement cuff can be produced at a low cost.

Note that with the fold-back type of cuff, due to the fact the inner cloth can be seen on the outside in the folded-back region near the leading end, if the air bladder were to be extended to the folded-back region, the cloth seen on the outside (inner cloth) would inflate outward (to the side opposite to the measurement site) needlessly when air is pumped into the air bladder with a pump for blood pressure measurement. For this reason, the amount of air supplied to the air bladder would increase, resulting in a reduction in the efficiency of pressurization. Also, the measurement subject would feel uneasy about the expansion being abnormal. Accordingly, with the fold-back type of cuff, there is an actual problem in that the air bladder cannot be extended beyond the fold-back fitting in the circumferential direction. Because of the restriction on the extension range in the circumferential direction of the air bladder, the range of dimensions in the circumferential direction of the measurement site set as specifications of the cuff is narrower. More specifically, since the air bladder cannot be extended to the folded-back region, the minimum circumference cannot be less than the dimension in the circumferential direction of the air bladder. Also, since the dimension in the circumferential direction of the air bladder is reduced such that it is smaller than the dimension in the circumferential direction of the belt-shaped body, the maximum circumference is restricted to a dimension that is relatively small (it is thought that the dimension in the circumferential direction of the air bladder usually needs to be about two-thirds or more of the maximum circumference applied to the cuff). Also, in order to obtain the needed compression force, the dimension in the width direction of the air bladder cannot be reduced, and the dimension in the width direction of the belt-shaped body also cannot be accordingly reduced.

Also, cuffs of a type that wrap in one direction along the circumferential direction around a measurement site and do not have the above-described ring or temporary fastening structure are widely used as cuffs for medical institutions. However, it is envisioned that such cuffs for medical institutions are attached to a measurement site of a patient (measurement subject) by a medical professional (doctor, nurse, or the like) using both hands, and it is difficult for a measurement subject to attach it himself or herself.

With a blood pressure measurement cuff according to an embodiment, the first and second sides of the ring each have a substantially plate-shaped portion, and the pair of connecting portions of the ring are bent or curved such that the plate-shaped portions of the first and second sides follow the circumferential direction of the measurement site.

During temporary fastening to the above-described left arm, the first side is attached to a region on the inner circumferential end side of the outer cloth by the ring attachment member, and therefore it is located near the measurement site. Also, using an operation in which the measurement subject pulls the outer circumferential end of the belt-shaped body downward with the right hand, the second side receives a force in a leftward and downward direction from the belt-shaped body, thus entering a state of being near the measurement site. Here, with the blood pressure measurement cuff according to the embodiment, the pair of connecting portions of the ring are bent or curved so that the plate-shaped portion of the second side follows the circumferential direction of the measurement site. Accordingly, even if the measurement subject reduces the force with which the right hand pulls after the above-described temporary fastening to the left arm, there is almost no leeway for the ring to rotate about the first side in a direction in which the second side approaches the measurement site due to the elastic force of the measurement site. Accordingly, a case in which the belt-shaped body loosens is more effectively suppressed.

Note that if the plate-shaped portions of the first and second sides conform with the same flat plane, during the above-described temporary fastening to the left arm, the second side will be farther from the measurement site than the first side is. As a result, when the measurement subject reduces the force with which the right hand pulls after the above-described temporary fastening to the left arm, there is leeway for the ring to rotate about the first side in a direction in which the second side approaches the measurement site due to the elastic force of the measurement site. Therefore, there is a possibility that the belt-shaped body will loosen.

With a blood pressure measurement cuff according to an embodiment, a gap between the first side and the second side of the ring is set to be narrower at a central portion corresponding to the center in a length direction of the first and second sides than at two remaining ends continuous with the central portion and be substantially equal to the thickness of the region continuous with the outer circumferential end of the belt-shaped body, and the temporary fastening structure is composed of the central portion of the ring and provides friction to a portion of the belt-shaped body passing through the ring so as to suppress a case in which the region continuous with the outer circumferential end of the belt-shaped body is pulled back through the ring by the elastic force of the measurement site.

In the specification, the "thickness" of the belt-shaped body refers to the thickness of the belt-shaped body itself, excluding the hook-and-loop fastener and the like. Also, if the thickness varies depending on the region of the belt-shaped body, it refers to the maximum thickness.

With the blood pressure measurement cuff according to the embodiment, the gap between the first side and the second side of the ring is set to be narrower at a central portion corresponding to the center in the length direction of the first and second sides than at two remaining ends continuous with the central portion, and to be substantially equal to the thickness of the region continuous with the outer circumferential end of the belt-shaped body. During the above-described temporary fastening to the left arm, the region continuous with the outer circumferential end of the belt-shaped body is pulled through the ring. At this time, the first side of the ring is retained by being attached to the region on the inner circumferential end side of the outer cloth, whereas the second side receives the force in the leftward and downward direction from the belt-shaped body and therefore bends leftward and downward. As a result, the gap between the first side and the second side widens mainly in the central portion from its original state (natural state). Accordingly, the region continuous with the outer circumferential end of the belt-shaped body is easily pulled through the ring without receiving much friction from the central portion of the ring.

On the other hand, if the measurement subject reduces the amount of force with which the right hand pulls after the above-described temporary fastening to the left arm, the gap between the first side and the second side of the ring, including the central portion, will return to its original state. Accordingly, even if the region continuous with the outer circumferential end of the belt-shaped body pulled through by the arm strength attempts to go back through the ring due to the elastic force of the measurement site, the central portion of the ring enters a state of applying friction to the portion of the belt-shaped body passing through the ring. The friction effectively suppresses a case in which the belt-shaped body loosens.

Note that when the measurement subject is to remove the cuff from the left arm, first, the hook-and-loop fastener provided on the region on the outer circumferential end side of the inner cloth is separated from the opposing portion of the outer cloth with the right hand (actual fixing removal). Next, the second side of the ring is pulled away from the first side with the right hand (temporary fastening removal). Upon doing so, the gap between the first side and the second side widens mainly at the central portion. Accordingly, the region continuous with the outer circumferential end of the belt-shaped body (including the region in which the hook-and-loop fastener is provided) is easily pulled back through the ring without receiving much friction from the central portion of the ring. Accordingly, the belt-shaped body becomes a cylinder that is sufficiently wider than the left arm. Thereafter, the cuff is removed from the left arm.

With a blood pressure measurement cuff according to an embodiment, at the central portion, the first side of the ring has a protrusion protruding in a direction of approaching the second side, and the protrusion defines the gap.

With the blood pressure measurement cuff according to the embodiment, the temporary fastening structure is easily configured.

Note that it is desirable that the two end portions of the ring are attached via the ring attachment member to the region on the inner circumferential side of the outer cloth.

With a blood pressure measurement cuff according to an embodiment, the direction in which the protrusion of the first side protrudes is a direction of approaching the second side and a direction such that a leading end of the protrusion is closer to the measurement site than a base of the protrusion in a state of being attached to the measurement site, and in a cross-sectional view along the length direction of the first or second side, an edge of the second side near the first side is formed into a substantially circular arc shape, and the leading end of the protrusion on the first side has a corner at a corner portion distant from the measurement site in a state of being attached to the measurement site, and has a curve at a corner portion located near the measurement site.

With the cuff according to the embodiment, when the measurement subject pulls the outer circumferential end of the belt-shaped body downward with the right hand for the above-described temporary fastening to the left arm, the region continuous with the outer circumferential end of the outer cloth of the belt-shaped body comes into contact with the edge of the second side near the first side so as to wrap around it, and the region continuous with the outer circumferential end of the inner cloth of the belt-shaped body comes into contact with the corner portion of the leading end of the protrusion near the measurement site. Here, in a cross-sectional view along the length direction of the first or second side, the edge of the second side near the first side is formed in a substantially circular arc shape. Accordingly, the region continuous with the outer circumferential end of the belt-shaped body is easily pulled through the ring without being caught on the edge of the second side near the first side. At this time, the gap between the first side and the second side of the ring widens as described above, and therefore, the corner portion (corner) distant from the measurement site on the leading end of the protrusion does not impede the pulling of the region continuous with the outer circumferential end of the belt-shaped body.

On the other hand, if the measurement subject reduces the force of pulling with the right hand after the above-described temporary fastening to the left arm, the portion wrapped around the edge of the second side near the first side starts to unbend, as a result of which the region continuous with the outer circumferential end of the inner cloth of the belt-shaped body strongly comes into contact with the corner portion distant from the measurement site on the leading end of the protrusion on the first side. Here, in a cross-sectional view along the length direction of the first or second side, the corner portion distant from the measurement site on the leading end of the protrusion has a corner. Accordingly, even if the region continuous with the outer circumferential end of the belt-shaped body pulled by the arm strength attempts to go back through the ring due to the elastic force of the measurement site, the region continuous with the outer circumferential end of the inner cloth of the belt-shaped body is caught on the corner of the corner portion distant from the measurement site on the leading end of the protrusion and receives a large amount of friction. Accordingly, a case in which the belt-shaped body loosens is more effectively suppressed.

With a blood pressure measurement cuff according to an embodiment, the thickness of the belt-shaped body is substantially uniform.

With the blood pressure measurement cuff according to the embodiment, the thickness of the belt-shaped body is substantially uniform, and therefore when the measurement subject pulls the outer circumferential end of the belt-shaped body downward with the right hand for the above-described temporary fastening to the left arm, the region continuous with the outer circumferential end of the belt-shaped body passes smoothly through the gap between the first side and the second side of the ring and is easily pulled out.

Note that it is sufficient that the region in which the hook-and-loop fastener for the belt-shaped body (the inner cloth) is provided (the region where the overall thickness of the cuff is greater than that of the belt-shaped body due to the thickness of the hook-and-loop fastener) is passed through the ring at a stage when the belt-shaped body is made into a cylinder that is sufficiently wider than the left arm. At this stage, the measurement subject can use both hands, and therefore, for example, the measurement subject can grip the ring with one hand and pull the outer circumferential end of the belt-shaped body (including the region in which the hook-and-loop fastener is provided) through the ring with the other hand. In such a case, even if a small amount of friction is received from the ring, the region in which the hook-and-loop fastener is provided on the belt-shaped body can be pulled. Also, the hook-and-loop fastener may be passed through the ring at the time of shipping the actual product. In such a case, even in the state of actual use, the hook-and-loop fastener prevents slippage through the ring, making it difficult to come out from the ring.

On the other hand, after the above-described temporary fastening to the left arm, when the measurement subject reduces the force of pulling with the right hand, the temporary fastening structure of the ring can reliably suppress a case in which the region continuous with the outer circumferential end of the belt-shaped body is pulled back through the ring, regardless of whether or not any portion of the belt-shaped body is located in the ring, or in other words, regardless of the dimension in the circumferential direction of the measurement site.

With a blood pressure measurement cuff according to an embodiment, the outer cloth of the belt-shaped body has raised fibers, and the raised fibers are down-grain with respect to the direction in which the region continuous with the outer circumferential end is pulled through the ring.

With the blood pressure measurement cuff according to the embodiment, the outer cloth of the belt-shaped body has raised fibers, and the raised fibers are down-grain with respect to the direction in which the region continuous with the outer circumferential end is pulled through the ring. Accordingly, when the measurement subject pulls the outer circumferential end of the belt-shaped body downward with the right hand for temporary fastening to the left arm, the region continuous with the outer circumferential end of the outer cloth of the belt-shaped body slides smoothly while wrapping around the side of the second side that faces the first side. Accordingly, the region continuous with the outer circumferential end of the belt-shaped body is easily pulled through the ring.

With a blood pressure measurement cuff according to an embodiment, the ring is composed of an integrally-molded plastic material.

With the blood pressure measurement cuff according to the embodiment, the ring is composed of a plastic material. Plastic materials are usually more flexible than metal. Accordingly, when the outer circumferential end of the belt-shaped body is passed through the ring so as to form a cylinder that is sufficiently wider than an arm, and when the measurement subject pulls the outer circumferential end of the belt-shaped body downward with the right hand for the above-described temporary fastening to the left arm, the gap between the first side and the second side of the ring widens more easily than in the case where the ring is composed of metal. Accordingly, the blood pressure measurement cuff can be attached more easily. Also, since the ring is composed of an integrally-molded plastic material, it can be produced at a lower cost and more easily than in the case where the ring is composed of metal.

Note that plastic materials usually have lower mechanical strength than metal. However, with the blood pressure measurement cuff (of the type that wraps in one direction around the measurement site), although arm strength is applied to the ring via the region that is continuous with the outer circumferential end of the belt-shaped body during the above-described temporary fastening, in the state of being attached after the actual fixing is complete, hardly any force (particularly force in the direction of widening the gap between the first side and the second side) is applied to the ring, even if air is pumped into the fluid bladder with a pump for blood pressure measurement. Accordingly, this leaves some amount of freedom in the design of the material qualities and shape of the ring. As a result, the ring can be formed using a variety of plastic materials. In contrast to this, with the fold-back type of blood pressure measurement cuff described above, when air is pumped into the air bladder with a pump for blood pressure measurement, a force (normally a force larger than the arm strength) is applied in the direction of widening the gap between the two opposing sides of the ring. For this reason, if the ring is made of a plastic material, there is a risk that it will break. Accordingly, with the fold-back type of blood pressure measurement cuff described above, it is difficult to form the ring using a plastic material.

With a blood pressure measurement cuff according to an embodiment, the ring attachment member has a cylindrical portion that surrounds portions of the first side of the ring other than the central portion.

With the blood pressure measurement cuff according to the embodiment, the ring attachment member has a cylindrical portion that surrounds portions of the first side of the ring other than the central portion. Accordingly, the ring can pivot about the first side. Accordingly, when starting the above-described attachment to the left arm, for example, the ring can be caused to stand with respect to the outer cloth such that the second side of the ring is distant from the outer cloth. Accordingly, it is easier for the outer circumferential end of the belt-shaped body to pass through the ring.

With a blood pressure measurement cuff according to an embodiment, raised fibers that can engage with the hook-and-loop fastener are provided on the outer circumferential surface of the ring attachment member.

With the blood pressure measurement cuff according to the embodiment, raised fibers that can engage with the hook-and-loop fastener are provided on the outer circumferential surface of the ring attachment member. Accordingly, during the above-described actual fixing, the region at which the hook-and-loop fastener is provided on the outer circumferential end side of the inner cloth opposes the region in which the ring attachment member is provided on the inner circumferential end side of the outer cloth, and the hook-and-loop fastener can engage with the raised fibers on the outer circumferential surface of the ring attachment member. As a result, the maximum circumference of the measurement site set as a specification of the cuff can be made larger.

The blood pressure measurement cuff attachment method of the present invention is a blood pressure measurement cuff attachment method for attaching the blood pressure measurement cuff according to any one of claims 1 to 10 such that a measurement site is wrapped in one direction along a circumferential direction, the blood pressure measurement cuff attachment method including:

an arrangement step of, with the outer cloth of the belt-shaped body on the outer side, passing the outer circumferential end of the belt-shaped body through the ring attached to the region on the inner circumferential side of the outer cloth so as to make the belt-shaped body into a cylinder that is wider than the measurement site, and, from a side at which the cylindrical cuff appears to a measurement subject to be in the form of a counterclockwise spiral when the measurement site is located on a left body half of the measurement subject, or from a side at which the cylindrical cuff appears to the measurement subject to be in the form of a clockwise spiral when the measurement site is located on a right body half of the measurement subject, passing the measurement site through the cylindrical belt-shaped body, the ring being adjusted so as to be located below the measurement site in the arrangement step;

a temporary fastening step of pulling the outer circumferential end of the belt-shaped body downward with a hand belonging to a body half opposite to a body half to which the measurement site belongs, so as to substantially eliminate a gap between the inner cloth of the belt-shaped body and the measurement site, and in the temporary fastening step, the ring allows the region continuous with the outer circumferential end of the belt-shaped body to be pulled by the arm strength of the hand through the ring, whereas a temporary fastening structure of the ring suppresses a case in which the region continuous with the outer circumferential end of the belt-shaped body pulled by the arm strength is pulled back through the ring by the elastic force of the measurement site; and an actual fixing step of bringing the region continuous with the outer circumferential end of the belt-shaped body along the circumferential direction of the measurement site into alignment with an orientation that is the same as that of a portion that has not passed through the ring of the belt-shaped body, so as to fix the hook-and-loop fastener provided on the region on the outer circumferential end side of the inner cloth to an opposing portion on the outer cloth.

According to the blood pressure measurement cuff attachment method of the present embodiment, no unnatural operation is required during attachment, unlike the case of using the above-described fold-back type of cuff. In particular, in the above-described temporary fastening step, the measurement subject need only temporarily pull the outer circumferential end of the belt-shaped body downward with the hand. The operation for temporary fastening is not an operation in which the hand moves in a direction heading further to the side away from the body, and there is no need for the measurement subject to continue to use his or her arm strength to maintain the tensile force of the belt-shaped body until the actual fixing step is complete. Accordingly, according to the blood pressure measurement cuff attachment method of the present invention, the measurement subject can easily attach the cuff to a measurement site by himself or herself. For example, an elderly person with little flexibility or a sick person with little arm strength can perform attachment relatively easily by himself or herself.

Advantageous Effects of Invention

As is evident from the above description, a measurement subject can easily attach the blood pressure measurement cuff of the present invention by himself or herself.

Also, according to the blood pressure measurement cuff attachment method of the present invention, the measurement subject can easily attach the cuff to a measurement site by himself or herself.

DESCRIPTION OF EMBODIMENTS

Hereinafter, an embodiment of the present invention will be described in detail with reference to the drawings.

Figure 1:
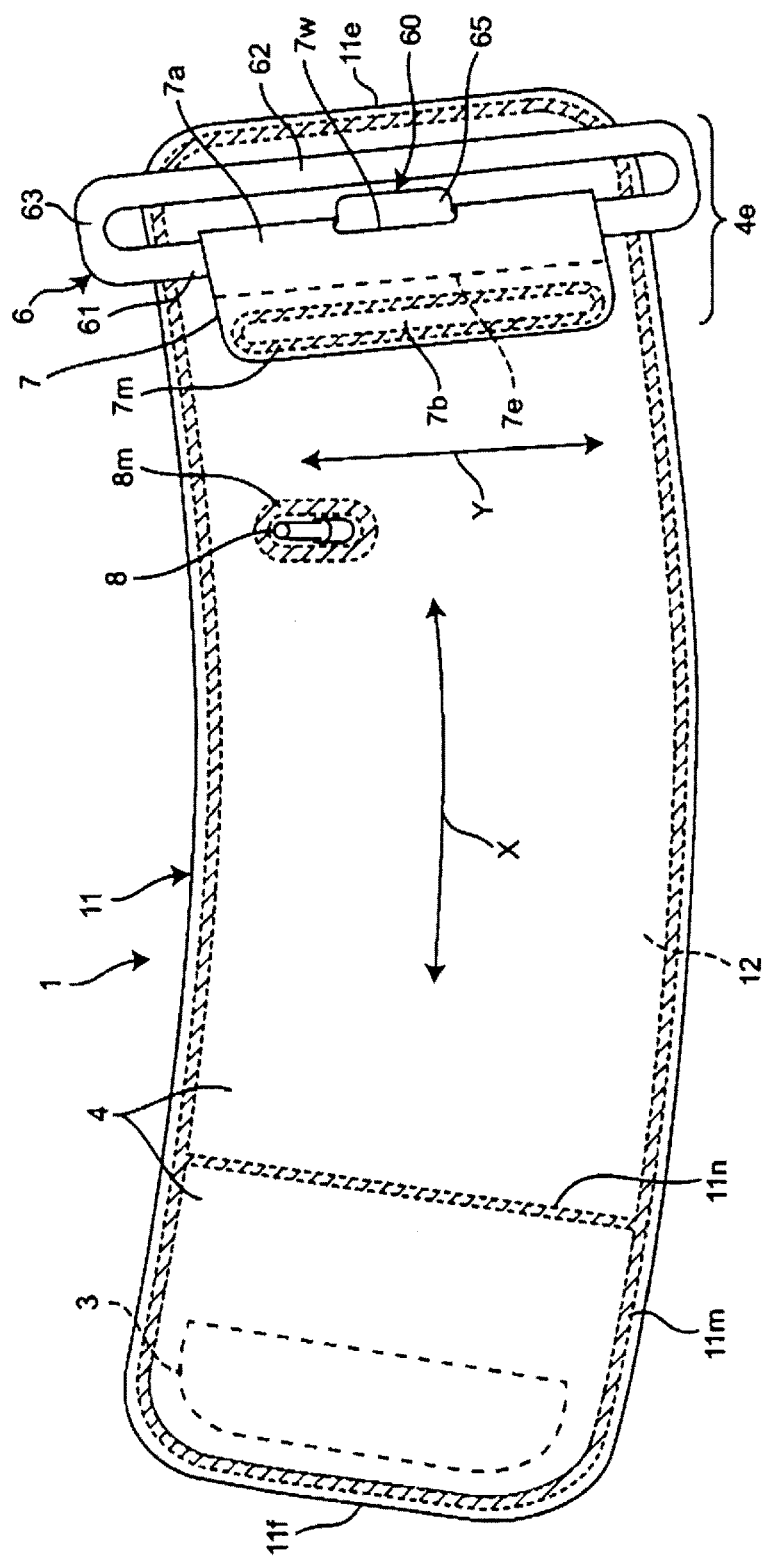
FIG. 1 is a plan view showing a blood pressure measurement cuff according to an embodiment of the present invention in an expanded state, in a view from an outer cloth side.
Figure 2:
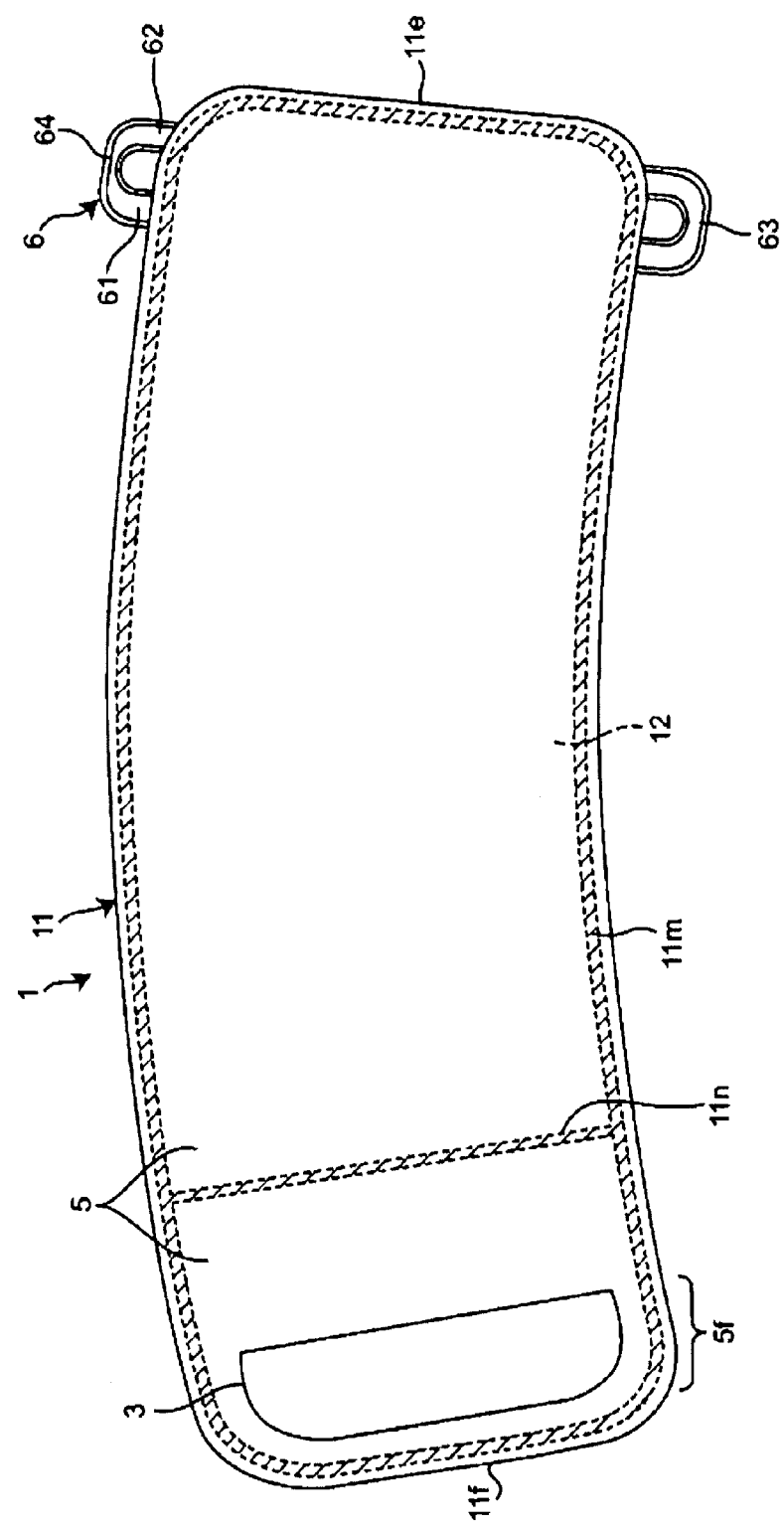
FIG. 2 is a plan view showing the cuff in an expanded state in a view from an inner cloth side.

FIGS. 1 and 2 show a blood pressure measurement cuff according to an embodiment of the present invention (denoted overall by reference numeral 1) in an expanded state, in a view from an outer cloth 4 side and an inner cloth 5 side, respectively. The cuff 1 is to be wrapped in one direction along the circumferential direction around a measurement site (e.g., the left arm).

The cuff 1 includes an elongated belt-shaped body 11 that extends in a substantially circular arc shape. In a state of being attached to the measurement site, the direction X in which in the belt-shaped body 11 extends is substantially the same as the circumferential direction of the measurement site (for this reason, the circumferential direction of the measurement site is indicated by the same reference numeral X where appropriate).

Figure 5:
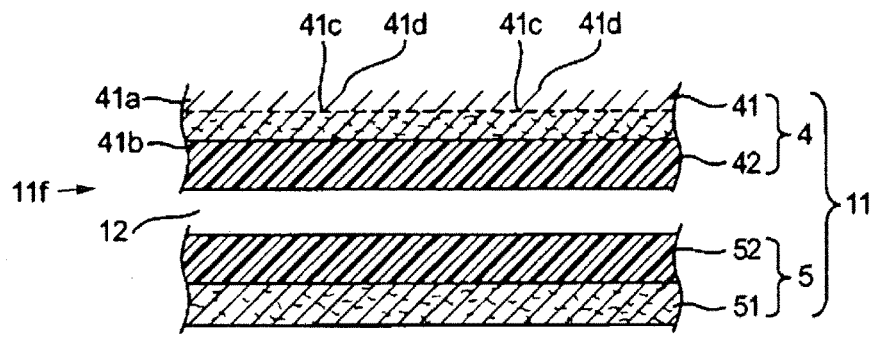
FIG. 5 is a diagram showing a cross-sectional structure of a belt-shaped body that forms the cuff.

The belt-shaped body 11 includes an inner cloth 5 (shown in FIG. 2) that is to be in contact with the measurement site, and an outer cloth 4 (shown in FIG. 1) that opposes the inner cloth 5. The peripheral edges of the inner cloth 5 and the outer cloth 4 are welded together along a ring-shaped line 11m so as to form a bag shape (welded regions are denoted by diagonal lines). In this example, as shown in FIG. 5, in order to compress the measurement site, the inner cloth 5 is composed of a sewn nylon cloth 51 with a large amount of elasticity, and a polyvinyl chloride (PVC) film 52 welded to the underside of the nylon cloth 51. The outer cloth 4 is composed of a sewn polyester cloth 41 with very little elasticity compared to the inner cloth 5 (substantially not elastic), and a PVC film 42 welded to the underside of the polyester cloth 41. The polyester cloth 41 includes a knitted fabric 41b and raised fibers 41a provided on the outside of the knitted fabric 41b. The raised fibers 41a are formed in a loop shape so as to engage with a later-described hook-andloop fastener (hook) 3. In a view from the outer circumferential end 11f, which will be described next, the raised fibers 41a are down-grain (peaks 41d of loops fall away from the outer circumferential end 11f with respect to bases 41c of loops).

As shown in FIGS. 1 and 2, the belt-shaped body 11 has an inner circumferential end 11e on the side that is to be inward and an outer circumferential end 11f on the side that is to be outward when wrapped in one direction (a spiral shape in a cross-sectional view along the length direction of the measurement site) along the circumferential direction around the measurement site. At a location near the outer circumferential end 11f of the belt-shaped body 11, the inner cloth 5 and the outer cloth 4 are welded together along a division line 11n that extends in a width direction Y that is perpendicular to the extension direction X. Accordingly, an air bladder 12 serving as a fluid bladder is partitioned by the dividing line 11n and the ring-shaped line 11m on the right side of the dividing line 11n in FIGS. 1 and 2, between the inner cloth 5 and the outer cloth 4. As a result, the thickness of the belt-shaped body 11 is substantially uniform.

A hook-and-loop fastener 3 is provided in a region 5f on the outer circumferential end 11f side of the inner cloth 5. The hook-and-loop fastener 3 has hook-shaped raised fibers (not shown) and can be detachably fixed to the outer cloth 4 (the raised fibers 41a thereof).

A ring 6 is attached via a ring attachment member 7 in a region 4e at the inner circumferential end 11e side of the outer cloth 4.

The ring 6 is composed of an integrally-molded plastic material (e.g., ABS resin (acrylonitrile butadiene styrene copolymer)) and includes a first side 61 that extends along the width direction Y of the belt-shaped body 11, a second side 62 that extends along the first side 61, and a pair of connecting portions 63 and 64 that connect the first and second sides 61 and 62. The region continuous with the outer circumferential end 11f of the belt-shaped body 11 is to be passed through the ring 6. Note that the first and second sides 61 and 62 may be attached slightly obliquely with respect to the width direction Y shown in FIG. 1.

Figure 3A:
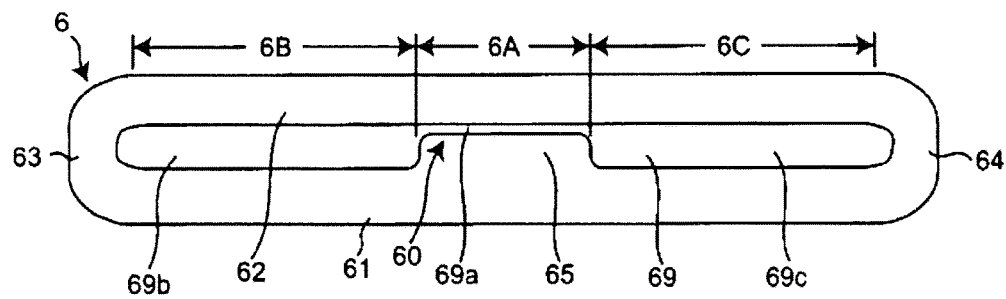
FIG. 3(A) is a diagram showing a ring of the cuff in a view from approximately the same side as in FIG. 1 (outside).
Figure 3B:
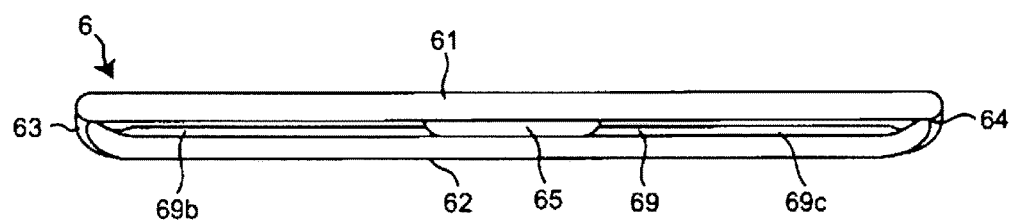
FIG. 3(B) is a diagram showing the ring shown in FIG. 3(A) in a view from below in FIG. 3(A) (from a lateral side).
Figure 3C:
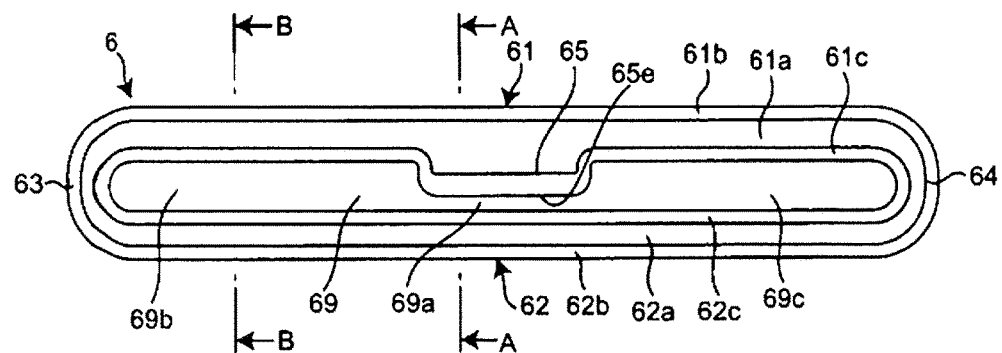
FIG. 3(C) is a diagram showing the ring of the cuff in a view from approximately the same side as in FIG. 2 (underside).

FIGS. 3(A) and 3(C) respectively show the ring 6 in views from roughly the same sides as in FIGS. 1 and 2 (outside and underside). FIG. 3(B) shows the ring 6 shown in FIG. 3(A) in a view from below in FIG. 3(A) (from the lateral side). Also, FIGS. 4(A) and 4(B) respectively show a cross-sectional view taken along line A-A and a cross-sectional view taken along line B-B in FIG. 3(C) (the broken lines in FIGS. 4(A) and 4(B) indicate the outline of the ring 6. The same follows for FIG. 10, which will be described later).

Figure 4B:
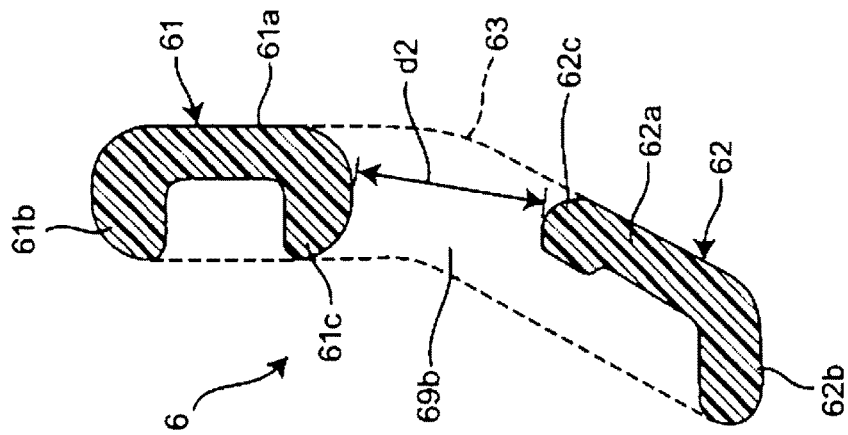
FIG. 4(B) is a diagram showing a cross-sectional view of the ring taken along line B-B in FIG. 3(C).

As shown in FIGS. 3(C) and 4(B), the first side 61 has a substantially plate-shaped portion 61a, and edges 61b and 61c that extend from the plate-shaped portion 61a to the underside. Also, the second side 62 has a substantially plate-shaped portion 62a and edges 62b and 62c that extend from the plate-shaped portion 62a to the underside.

Figure 4A:
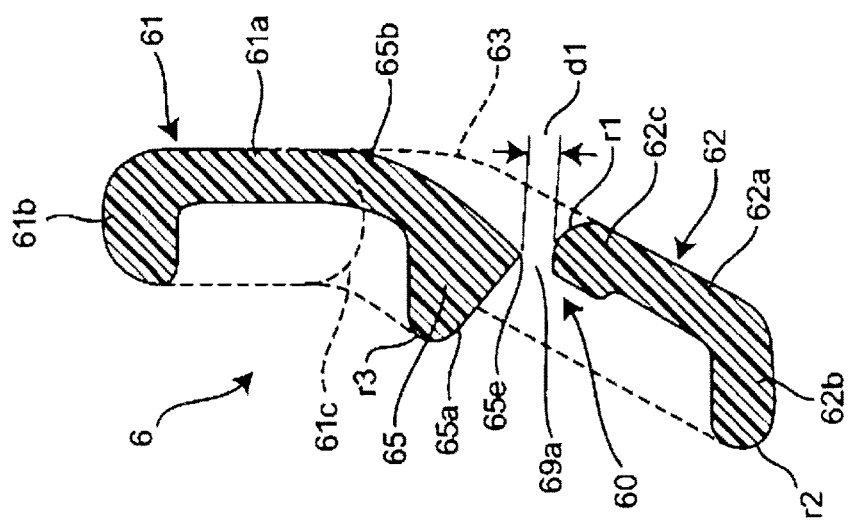
FIG. 4(A) is a diagram showing a cross-sectional view of the ring taken along line A-A in FIG. 3(C).

As can be well understood from FIGS. 4(A) and 4(B), the connecting portion 63 of the ring 6 is bent or curved such that the outside is peak-shaped and the underside is trough-shaped. The same follows for the connecting portion 64 as well. Accordingly, in a state of being attached to the measurement site (the left arm 90 shown in FIG. 10 in this example), the plate-shaped portions 61a and 62a of the first and second sides 61 and 62 can follow the circumferential direction X of the measurement site.

As can be well understood from FIGS. 3(A) and 3(C), the first side 61 of the ring 6 has a protrusion 65 protruding in the direction approaching the second side 62 at a central portion 6A that corresponds to the center in the length direction of the first and second sides 61 and 62. More specifically, in a state of being attached to the measurement site (the left arm 90 shown in FIG. 10 in this example), the direction in which the protrusion 65 on the first side 61 protrudes is a direction of approaching the second side 62 and a direction such that the leading end 65a of the protrusion 65 is closer to the measurement site than the base 65b of the protrusion.

Due to the existence of the protrusion 65, a gap 69 between the first side 61 and the second side 62 is narrower at the central portion 6A than at both remaining ends 6B and 6C continuous with the central portion 6A. As shown in FIG. 4(A), the dimension of the gap 69a at the central portion 6A (nearest distance) is set to d1. The dimension d1 of the gap 69a is set to be substantially equal to the thickness of the belt-shaped body 11. As shown in FIG. 4(B), the dimension of a gap 69b at the end 6B is set to d2 (>d1), which is equal to the dimension of a gap 69c at the end 6C.

In this way, a temporary fastening structure 60 is simply configured due to the protrusion 65 at the central portion 6A of the ring 6 defining the closest distance d1 (gap 69a) between the first side 61 and the second side 62. When performing temporary fastening, which will be described later, the temporary fastening structure 60 applies friction to the portion of the belt-shaped body 11 that passes through the ring 6 (gap 69a of central portion 6A) so as to suppress a case in which the region continuous with the outer circumferential end 11 of the belt-shaped body 11 is pulled back through the ring 6 by the elastic force of the measurement site.

Here, as shown in FIG. 4(A), the edge 62c of the second side 62, which is near the first side 61, has a shorter dimension extending to the underside than the edge 62b on the opposite side, and is formed in an approximate semi-circular arc shape (curve r1 is formed). Also, a curve r2 is formed on the leading end of the edge 62b. The leading end 65a of the protrusion 65 on the first side 61 has a corner 65e at a corner portion that is distant from the measurement site (the left arm 90 shown in FIG. 10 in this example) in the state of being attached to the measurement site, whereas a curve r3 is formed at the corner portion near the measurement site.

Figure 10:
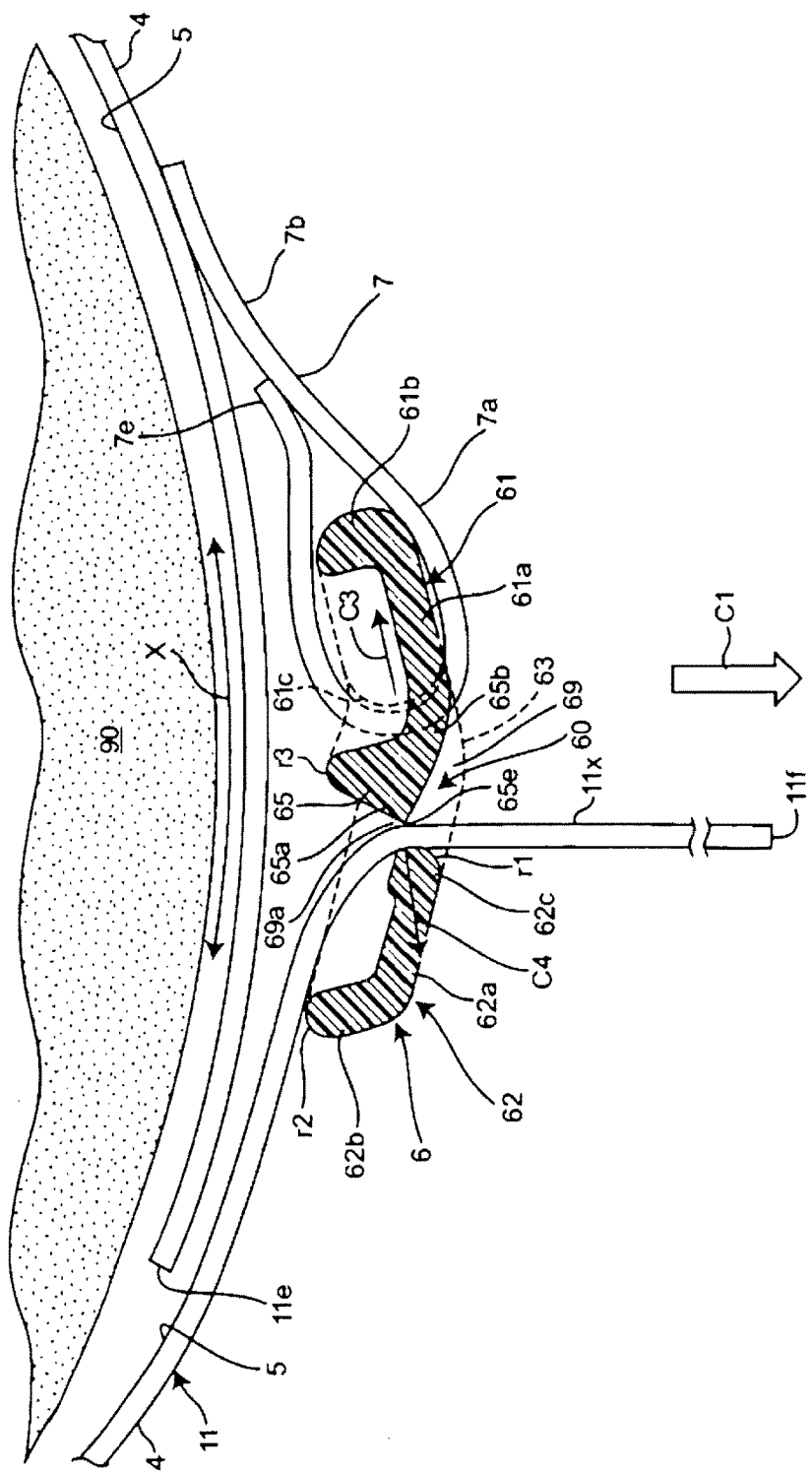
FIG. 10 is a diagram in which the vicinity of the ring in FIG. 8 is shown enlarged.

As can be understood from FIGS. 1 and 10, the ring attachment member 7 includes a cylindrical portion 7a having a hole 7w, and a flat portion 7b that is continuous with the tube-shaped portion 7a and is attached to the outer cloth 4. The tube-shaped portion 7a surrounds portions of the first side 61 of the ring 6 other than the protrusion 65 at the central portion (corresponds to both ends 6B and 6C). The protrusion 65 of the ring 6 is exposed through the hole 7w.

In this example, the ring attachment member 7 is formed by a cloth material that is the same as that of the polyester cloth 41 that forms the outer cloth 4 (includes knit fabric 41b and raised fibers 41a provided on the outside of the knit fabric 41b) being folded back so as to surround the first side 61 of the ring 6 as shown in FIG. 10, and sewing the leading end 7e to the flat portion 7b. As a result, the portion that is visible on the outside of the ring attachment member 7 (raised fibers on the outer circumferential surface) can engage with the hook-and-loop fastener 3. The flat portion 7b is fixed by being welded to the region 4e on the inner circumferential end 11e side of the outer cloth 4 as shown in FIG. 1 (denoted by diagonal lines at the welded region 7m).

As a result of the ring 6 being attached using the ring attachment member 7, the ring 6 can pivot about the first side 61. Accordingly, when starting attachment to the measurement site, for example, the ring 6 can be caused to stand with respect to the outer cloth 4 such that the second side 62 of the ring 6 is distant from the outer cloth 4. This makes it easier to pass the outer circumferential end 11*f* of the belt-shaped body 11 through the ring 6.

Also, the outer cloth 4 of the belt-shaped body 11 is provided with a nipple 8 for performing supply of air to and discharge of air from the air bladder 12. The nipple 8 is attached at approximately the central portion of the outer cloth 4 (denoted by diagonal lines at welded region 8*m*). An air tube 88 shown in FIG. 7 is attached to the nipple 8.

Figure 6:
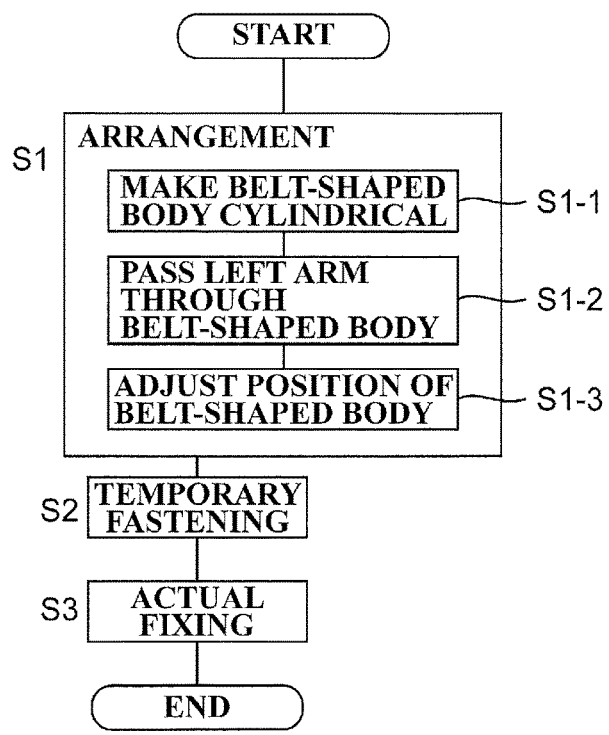
FIG. 6 is a diagram showing a flow of an attachment method for attaching the cuff to a left arm serving as a measurement site.

FIG. 6 shows a flow for an attachment method for attaching the cuff 1 to the left arm 90 serving as the measurement site. The attachment method is roughly executed by the measurement subject in the following order: arrangement step S1, temporary fastening step S2, and actual fixing step S3.

Figure 7:
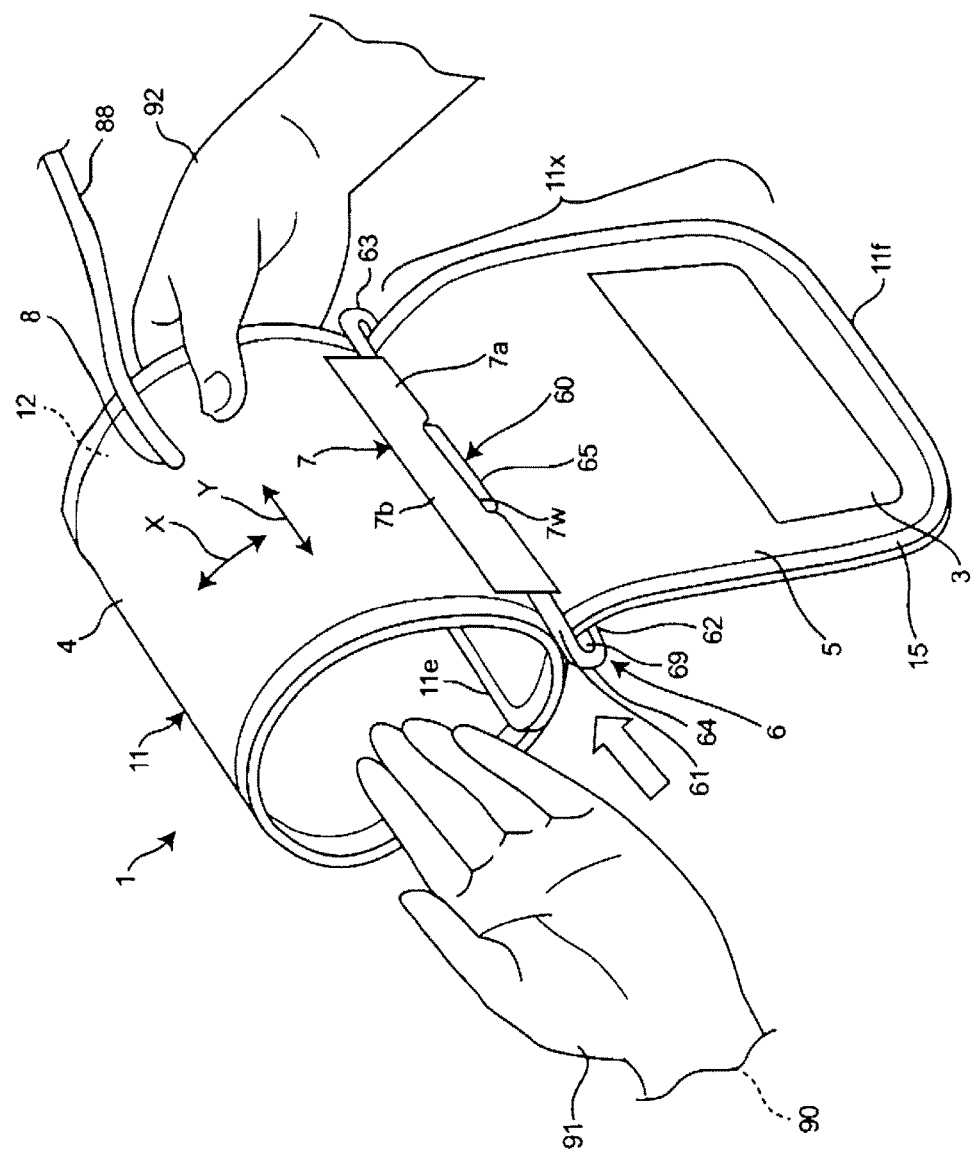
FIG. 7 is a diagram showing a state of carrying out an arrangement step in the attachment method.

(1) In arrangement step S1, as shown in FIG. 7, first, with the outer cloth 4 of the belt-shaped body 11 on the outer side, the measurement subject passes the outer circumferential end 11*f* of the belt-shaped body 11 through the ring 6 attached to the region on the inner circumferential end 11*e* of the outer cloth 4, making the belt-shaped body 11 into a cylinder that is sufficiently wider than the left arm 90 (step S1-1 in FIG. 6).

At this stage, the region in which the hook-and-loop fastener 3 is provided on the inner cloth 5 of the belt-shaped body 11 (region of the cuff that is thicker overall than the belt-shaped body 11 itself due to the amount of thickness of the hook-and-loop fastener 3) is passed through the ring 6. At this stage, the measurement subject can use both hands, and therefore, for example, the ring 6 is gripped with the left hand 91, and the outer circumferential end 11*f* of the belt-shaped body 11 (including the region at which the hook-and-loop fastener 3 is provided) can be pulled through the ring 6 using the right hand 92. In this case, even if a small amount of friction is received from the ring 6, the region at which the hook-and-loop fastener 3 of the belt-shaped body 11 is provided can be pulled. Also, the hook-and-loop fastener 3 may be passed through the ring 6 at the time of shipping the actual product. In such a case, even in the state of actual use, the hook-and-loop fastener 3 prevents slippage through the ring 6, making it difficult to come out from the ring 6.

Next, the left hand 91 or left arm 90 is passed through the cylindrical belt-shaped body 11 from the side at which the cylindrical belt-shaped body 11 appears to the measurement subject to be in a counterclockwise spiral shape (counterclockwise from the inner circumferential end 11*e* to the outer circumferential end 11*f*) (step S1-2 in FIG. 6).

Next, the belt-shaped body 11 is adjusted so as to surround the upper portion of the left arm 90 and so that the ring 6 is positioned almost directly below the upper portion of the left arm (step S1-3 in FIG. 6). Note that it is sufficient that the ring 6 is positioned below the upper portion of the left arm, even if it is not exactly directly below the upper portion of the left arm. In actuality, the position of the air tube 88 is positioned on the upper side. Alternatively, it is possible to attach a mark to the cuff 1 (belt-shaped body 11) and align it with the center of the arm, for example, or the like. The position is determined by the arrangement of the air bladder according to which the position of the pulse in the upper arm can be accurately compressed. If the cuff is attached at the correct position, with the structure of the cuff 1, the ring 6 will be located downward from the inner side of the arm.

By doing so, the left arm 90 is positioned in the cylindrical belt-shaped body 11.

Figure 8:
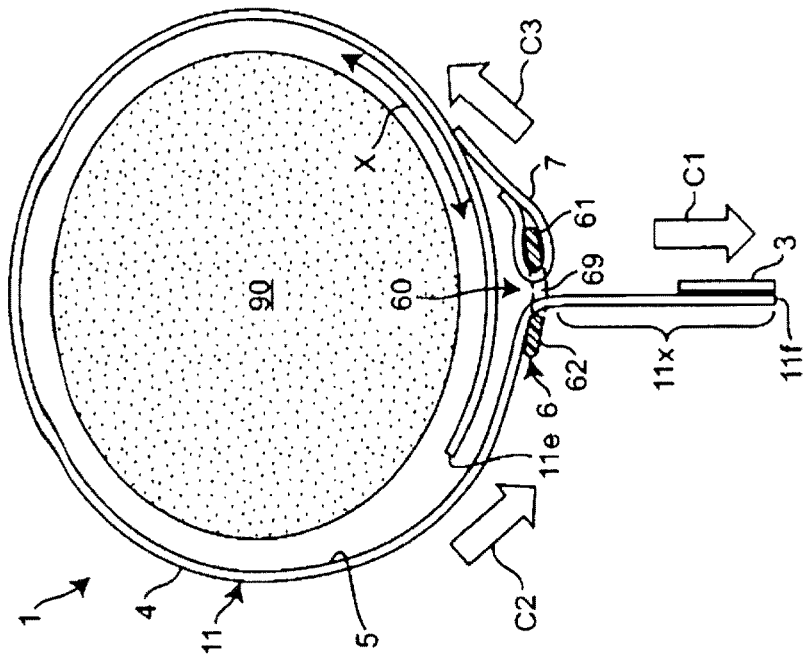
FIG. 8 is a diagram showing a state of carrying out a temporary fastening step in the attachment method.

(2) In the temporary fastening step S2, as shown in FIG. 8, the measurement subject temporarily pulls the outer circumferential end 11*f* of the belt-shaped body 11 in a downward direction C1 with the right hand 92, substantially eliminating the gap between the inner cloth 5 of the belt-shaped body 11 and the left arm (this operation will be referred to as "temporary fastening" where appropriate). Temporary fastening is completed by the measurement subject merely temporarily pulling the outer circumferential end 11*f* of the belt-shaped body 11 in the downward direction C1 with the right hand 92.

At this time, the ring 6 allows the region 11*x* continuous with the outer circumferential end 11*f* of the belt-shaped body 11 to be pulled through the ring 6 in the downward direction C1 (direction away from the left arm 90) with the arm strength of the right hand 92. On the other hand, the temporary fastening structure 60 of the ring 6 suppresses a case in which the region 11*x* continuous with the outer circumferential end 11*f* of the belt-shaped body 11 pulled through using the arm strength of the right hand 92 is pulled back through the ring 6 by the elastic force of the left arm 90. Accordingly, even if the measurement subject reduces the force with which the right hand 92 pulls, a case in which the belt-shaped body 11 loosens is suppressed. Note that arrows C2 and C3 in FIG. 8 respectively indicate the tensile force received by the belt-shaped body 11 and the ring attachment member 7 due to the arm strength of the right hand 92.

Specifically, with the cuff 1, as described above, due to the presence of the protrusion 65 at the central portion 6A, the gap 69 between the first side 61 and the second side 62 of the ring 6 is narrower than the remaining end portions 68 and 6C that are continuous with the central portion 6A. Moreover, the dimension (closest distance) d1 of the gap 69*a* at the central portion 6A is set to be substantially equal to the thickness of the belt-shaped body 11. Here, as shown schematically in FIG. 10, when the region 11*x* that is continuous with the outer circumferential end 11*f* of the belt-shaped body 11 is pulled through the ring 6 during temporary fastening to the left arm, the first side 61 of the ring 6 is attached to the region 4*e* on the inner circumferential end 11*e* side of the outer cloth 4 by the ring attachment member 7 and is held by receiving a tensile force C3. In contrast to this, the second side 62 receives a force in a leftward and downward direction (indicated by reference numeral C4) from the belt-shaped body 11, and therefore bends leftward and downward. As a result, the gap 69 between the first side 61 and the second side 62 widens mainly at the central portion 6A from its original state (natural state). Accordingly, the region 11*x* continuous with the outer circumferential end 11*f* of the belt-shaped body 11, is easily pulled through the ring 6 without receiving much friction from the protrusion 65 at the central portion 6A of the ring 6.

In particular, with the cuff 1, when the measurement subject pulls the outer circumferential end 11*f* of the belt-shaped body 11 in the downward direction C1 for temporary fastening to the left arm, the region 11*x* continuous with the outer circumferential end 11*f* of the outer cloth 4 of the belt-shaped body 11 comes into contact with the edge 62*c* of the second side 62, which is near the first side 61, so as to wrap around it, and the region 11*x* continuous with the outer circumferential end 11*f* of the inner cloth 5 of the belt-shaped body 11 comes into contact with the corner portion (corner 65*e*) of the leading end 65*a* of the protrusion 65, which is near the left arm 90. Here, in a cross-sectional view taken along the length direction of the first side 61 or the second side 62 (FIG. 10), the edge 62c of the second side 62 near the first side 61 is formed in a substantially circular arc shape and has a curve r1. Accordingly, the region 11x continuous with the outer circumferential end 11f of the belt-shaped body 11 is easily pulled through the ring 6 without catching on the edge 62c of the second side 62 near the first side 61. Also, the curve r2 formed on the leading end of the edge 62b of the second side 62, which is distant from the first side 61, and the curve r3 formed on the corner portion of the leading end 65a of the protrusion 65 of the first side 61, which is near the measurement site, prevent catching of the region 11x continuous with the outer circumferential end 11f of the belt-shaped body 11. At this time, as described above, the gap 69 between the first side 61 and the second side 62 widens, and therefore the corner portion (corner 65e) of the leading end 65a of the protrusion does not impede the pulling of the region 11x continuous with the outer circumferential end 11f of the belt-shaped body 11.

Also, with the cuff 1, since the thickness of the belt-shaped body 11 is substantially uniform, when the measurement subject pulls the outer circumferential end 11f of the belt-shaped body 11 in the downward direction C1 with the right hand 92 for the above-described temporary fastening to the left arm, the region 11x continuous with the outer circumferential end 11f of the belt-shaped body 11 smoothly passes through the gap 69 between the first side 61 and the second side 62 of the ring 6, and is thereby more easily pulled out.

Also, with the cuff 1, the outer cloth 4 of the belt-shaped body 11 has the raised fibers 41a, and the raised fibers 41a is aligned with the direction in which the region 11x continuous with the outer circumferential end 11f is pulled through the ring 6. Accordingly, when the measurement subject pulls the outer circumferential end 11f of the belt-shaped body 11 with the right hand 92 in the downward direction C1 for temporary fastening to the left arm, the region 11x continuous with the outer circumferential end 11f of the outer cloth 4 of the belt-shaped body 11 slides smoothly while wrapping around the side of the second side 62 that faces the first side 61. Accordingly, the region 11x continuous with the outer circumferential end 11f of the belt-shaped body 11 is more easily pulled through the ring 6.

On the other hand, after temporary fastening to the left arm, if measurement subject reduces the force of pulling with the right hand 92, the gap 69 between the first side 61 and the second side 62 of the ring 6 returns to its original state, including the central portion 6A. Also, if the measurement subject reduces the force of pulling with the right hand 92 after the temporary fastening to the left arm, the portion wrapped around the edge of the second side 62 near the first side 61 starts to unbend, and the region 11x continuous with the outer circumferential end 11f of the inner cloth 5 of the belt-shaped body 11 strongly comes into contact with the corner portion (corner 65e), which is distant from the left arm 90, on the leading end of the protrusion of the first side 61. Accordingly, even if the region 11x continuous with the outer circumferential end 11f of the belt-shaped body 11 pulled with the arm strength of the right arm 92 attempts to go back through the ring 6 due to the elastic force of the left arm 90, the protrusion 65 of the central portion 6A of the ring 6 enters a state of applying a large amount of friction to the region 11x continuous with the outer circumferential end 11f of the belt-shaped body 11. The friction effectively suppresses a case in which the belt-shaped body 11 loosens.

Also, with the cuff 1, the thickness of the belt-shaped body 11 is substantially uniform. Therefore, when the force with which the measurement subject pulls using the right hand 92 is reduced after the above-described temporary fastening to the left arm, the temporary fastening structure 60 of the ring 6 can reliably suppress a case in which the region 11x continuous with the outer circumferential end 11f of the belt-shaped body 11 is pulled back through the ring 6, regardless of the portion of the belt-shaped body 11 that is located in the ring 6, or in other words, regardless of the dimension in the circumferential direction X of the left arm 90.

Also, during the above-described temporary fastening to the left arm, the first side 61 is attached to the region 4e on the inner circumferential end 11e side of the outer cloth 4 using the ring attachment member 7, and therefore is located near the left arm 90. Also, according to an operation in which the measurement subject pulls the outer circumferential end 11f of the belt-shaped body 11 in the downward direction C1 with the right hand 92, the second side 62 receives a force C4 in an orientation that is downward and to the left from the belt-shaped body 11, and enters a state of being near the left arm 90. Here, with the cuff 1, a pair of connecting portions of the ring 6 are bent or curved such that the plate-shaped portions 61a and 62a of the first and second sides 61 and 62 follow the circumferential direction X of the left arm 90. Accordingly, after the temporary fastening to the left arm, even if the measurement subject reduces the force of pulling with the right hand 92, there is hardly any leeway for the ring 6 to rotate about the first side 61 in an orientation in which the second side 62 is in contact with the left arm 90 due to the elastic force of the left arm 90. Accordingly, a case in which the belt-shaped body 11 loosens is more effectively suppressed.

Note that if the plate-shaped portions 61a and 62a of the first and second sides 61 and 62 were to conform with the same flat plane, the second side 62 would be further from the left arm 90 than the first side 61 would be during the above-described temporary fastening to the left arm. As a result, after the above-described temporary fastening to the left arm, when the force with which the measurement subject pulls using the right hand 92 is reduced, there would be leeway for the ring 6 to rotate around the first side 61 in an orientation in which the second side 62 is in contact with the left arm 90 due to the elastic force of the left arm 90. Therefore, there would be a possibility that the belt-shaped body 11 will loosen.

Figure 9:
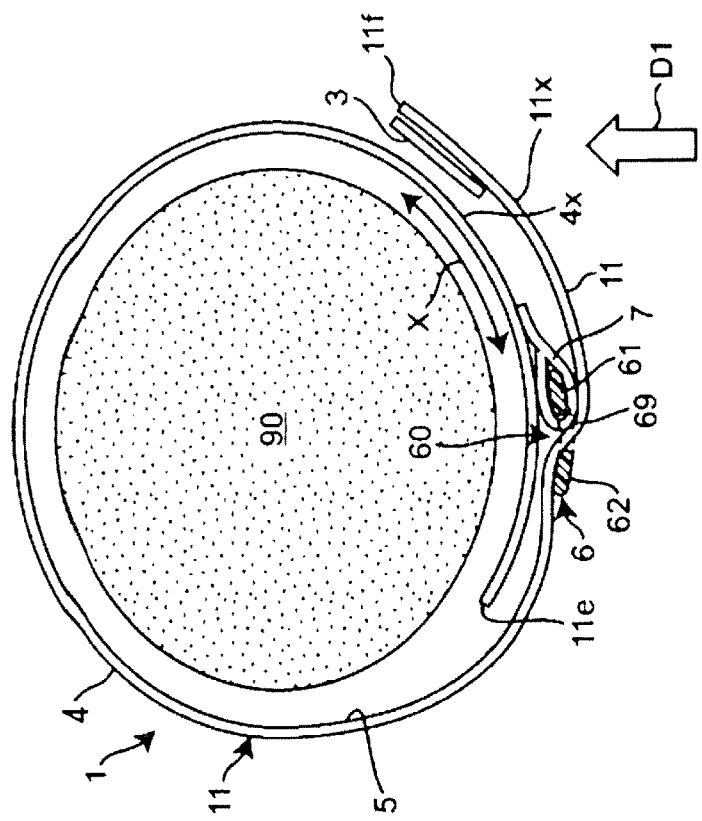
FIG. 9 is a diagram showing a state of carrying out an actual fixing step in the attachment method.

(3) In actual fixing step S3, as shown in FIG. 9, the measurement subject moves the right hand 92 in an upward direction D1 at the torso side of the left arm 90 and, along the circumferential direction X of the left arm, brings the region 11x continuous with the outer circumferential end 11f of the belt-shaped body 11 into alignment with an orientation that is the same as that of the portion that has not passed through the ring 6 of the belt-shaped body 11. Accordingly, the hook-and-loop fastener 3 provided on the region 5f on the outer circumferential end 11f side of the inner cloth 5 is fixed to the portion 4x opposing the outer cloth 4 (this operation is referred to as "actual fixing" as appropriate).

Thus, the cuff 1 is attached in one direction along the circumferential direction X to the left arm 90 serving as the measurement site. That is to say, when viewed by the measurement subject along the length direction of the left arm 90, it is attached in a counterclockwise spiral shape.

Thus, the blood pressure measurement cuff 1 does not require an unnatural operation during attachment, unlike the case of the fold-back type of cuff 1 described above. In particular, during the above-described temporary fastening to the left arm, the measurement subject need only temporarily pull the outer circumferential end 11*f* of the belt-shaped body 11 in the downward direction C1 with the right hand 92. The operation for temporary fastening is not an operation in which the hand moves further laterally from the lateral side of the body, and there is no need for the measurement subject to continue to use his or her arm strength to maintain the tensile force of the belt-shaped body 11 until the actual fixing is complete. Accordingly, a measurement subject can easily attach the blood pressure measurement cuff 1 by himself or herself. For example, an elderly person with little flexibility or a sick person with little arm strength can perform attachment relatively easily.

In the state of being attached after the actual fixing is complete, air is pumped into or discharged from the air bladder 12 with a pump through the air tube 88 shown in FIG. 7, and the blood pressure is measured using the oscillometric method (in which the cuff itself measures change in the pulsewave as a pressure sensor), for example. Note that a microphone may be built into the cuff 1 (belt-shaped body 11) so as to measure the blood pressure based on a pulse sound observed using the microphone, according to the Korotkoff method.

Also, in the state of being attached after the actual fixing is complete, the blood pressure measurement cuff 1 is wrapped around the left arm 90 in one direction along the circumferential direction X. In other words, in the entire region along the circumferential direction X of the left arm 90, the inner cloth 5 is hidden, and only the outer cloth 4 can be seen on the outside. As described above, the outer cloth 4 is set such that it has less elasticity than the inner cloth 5 (or is not elastic). In this case, when air is pumped into the air bladder 12 with a pump for blood pressure measurement, with the blood pressure measurement cuff 1, the cloth seen on the outside (outer cloth 4) does not needlessly inflate outward (to the side opposite to the left arm 90). Accordingly, it is possible to suppress the amount of air supplied to the air bladder 12, thereby increasing the efficiency of pressurization.

Also, with the blood pressure measurement cuff 1, the cloth seen on the outside (outer cloth 4) never needlessly inflates outward, and therefore the measurement subject is never caused to feel uneasy.

Furthermore, with the blood pressure measurement cuff 1, since the cloth seen on the outside (outer cloth 4) never needlessly inflates outward, an arrangement is possible in which the air bladder 12 is extended over most of the region in the circumferential direction X (length direction) in the belt-shaped body 11. With this kind of arrangement, there is no longer a restriction on the extension range of the air bladder in the circumferential direction in the case of a fold-back type of cuff (described above), whereby the range of dimensions in the circumferential direction of the measurement site set as specifications of the cuff 1 (refers to a range ranging from the minimum circumference to the maximum circumference) can be widened.

Also, with the cuff 1, raised fibers that can engage with the hook-and-loop fastener 3 are provided on the outer circumferential surface of the ring attachment member 7. Accordingly, during the above-described actual fixing, the region in which the hook-and-loop fastener 3 is provided on the outer circumferential end 11*f* side of the inner cloth 5 opposes the ring attachment member 7 on the inner circumferential end 11*e* side of the outer cloth 4, and the hook-and-loop fastener 3 can engage with the raised fibers on the outer circumferential surface of the ring attachment member 7. As a result, the maximum circumference of the measurement site set as a specification of the cuff 1 can be made even larger.

For example, if the range of dimensions in the circumferential direction of the measurement site ranges between 22 cm and 32 cm in the specifications of the fold-back type of cuff, the range of dimensions in the circumferential direction of the measurement site can be widened to 17 cm to 36 cm, for example, in the specifications of the cuff 1.

Also, it is known that the compression force compressing the artery of the left arm 90 relies on the dimension in the circumferential direction X of the air bladder 12 and the dimension in the width direction Y that intersects the circumferential direction X. The larger the dimension in the circumferential direction and the dimension in the width direction of the air bladder 12 are, the larger the compression force is. Here, as shown in FIGS. 1 and 2, according to the arrangement in which the air bladder 12 is extended over most of the region in the circumferential direction X, the dimension in the width direction of the air bladder 12 can be reduced instead in order to obtain the needed compression force. If the dimension in the width direction of the air bladder 12 is thus reduced, and the dimension in the width direction of the belt-shaped body 11 is accordingly reduced, the measurement subject can more easily attach the blood pressure measurement cuff 1. For example, assuming the dimension in the width direction of the cuff is 125 mm in the specifications of the fold-back type of cuff, in the specifications of the cuff 1, the dimension in the width direction of the cuff (belt-shaped body) can be reduced to 115 mm, for example. Also, if the dimensions in the width direction of the air bladder 12 and the belt-shaped body 11 are reduced, the cost of materials can be reduced. Accordingly, the blood pressure measurement cuff 1 can be produced at a low cost.

Also, with the cuff 1, the ring 6 is composed of a plastic material (e.g., ABS resin). Plastic materials are usually more flexible than metal. Accordingly, when the outer circumferential end 11*f* of the belt-shaped body 11 is passed through the ring 6 so as to form a cylinder that is sufficiently wider than the left arm 90 as shown in FIG. 7, and when the measurement subject pulls the outer circumferential end 11*f* of the belt-shaped body 11 in the downward direction C1 with the right hand 92 for the above-described temporary fastening to the left arm, the gap 69 between the first side 61 and the second side 62 of the ring 6 widens more easily than in the case when the ring 6 is composed of metal. Accordingly, the blood pressure measurement cuff 1 can be attached more easily. Also, since the ring 6 is composed of an integrally-formed plastic material, it can be produced at a lower cost and more easily than in the case where the ring 6 is composed of metal.

Note that plastic materials usually have lower mechanical strength than metal. However, with the blood pressure measurement cuff 1 (type wrapped in one direction around the measurement site), although a bit of arm strength is applied to the ring 6 via the region 11*x* that is continuous with the outer circumferential end 11*f* of the belt-shaped body 11 during the above-described temporary fastening, in the state of being attached after the actual fixing is complete, hardly any force (force in the direction of widening the gap 69 between the first side 61 and the second side 62) is applied to the ring 6, even if air is pumped into the air bladder 12 with a pump for blood pressure measurement. Accordingly, this leaves some amount of freedom in the design of the material qualities and shape of the ring 6. As a result, the ring 6 can be formed using various kinds of plastic materials.

When the measurement subject removes the cuff 1 from the left arm 90, first, the measurement subject separates the hook-and-loop fastener 3 provided on the region 5f on the outer circumferential end 11f side of the inner cloth 5 from the opposing portion on the outer cloth 4 with the right hand 92 (actual fixing removal). Next, the measurement subject pulls the second side 62 of the ring 6 away from the first side 61 with the right hand 92 (temporary fastening removal). Upon doing so, the gap 69 between the first side 61 and the second side 62 widens mainly at the central portion 6A. Accordingly, the region 11x that is continuous with the outer circumferential end 11f of the belt-shaped body 11 is more easily pulled through the ring 6 without receiving much friction from the central portion 6A of the ring 6. Accordingly, the belt-shaped body 11 becomes a cylinder that is sufficiently wider than the left arm. Thereafter, the cuff 1 is removed from the left arm.

Note that if the right arm is to be used as the measurement site instead of the left arm 90, it is sufficient that a cuff with a left-right inverted structure is created and the above description of the method for attachment to the left arm and the method for removal are read replacing "left" with "right". Also, it is sufficient that the measurement site is a site that can be wrapped by the cuff 1, and for example, it may be a wrist or a leg.

Figure 11:
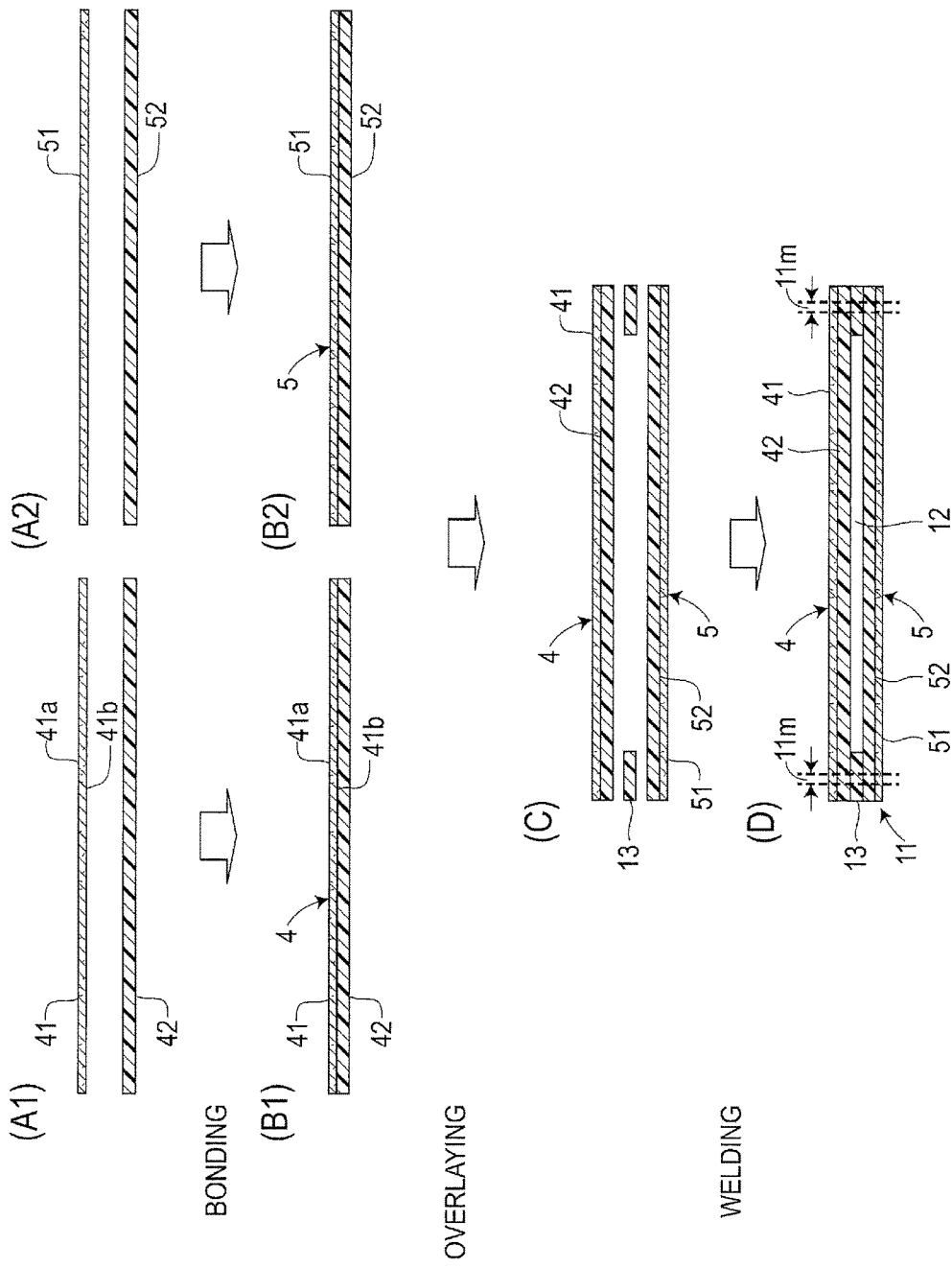
FIG. 11 is a process diagram illustrating a method of manufacturing the cuff.

FIG. 11 shows a method for manufacturing the cuff 1 (these drawings correspond to cross-sections taken along the width direction Y in FIG. 1).

First, as shown in FIG. 11, the above-described polyester cloth 41 and PVC film 42 are prepared as materials for the outer cloth 4, and the PVC film 42 is bonded to the underside (knitted fabric 41b side) of the polyester cloth 41. In addition to this, as shown in FIG. 11, the above-described nylon cloth 51 and PVC film 52 are prepared as materials for the inner cloth 5, and the PVC film 52 is bonded to the underside of the nylon cloth 51.

Note that at this stage, the nipple 8 and the ring attachment member 7 shown in FIG. 1 are attached to the outer cloth 4.

Next, as shown in FIG. 11, the inner cloth 5 and the outer cloth 4 are overlaid opposite each other via a reinforcing sheet 13 composed of PVC film. The shape of the reinforcing sheet 13 is a shape that is approximately the same as the regions 11m and 11n denoted by diagonal lines in FIG. 1 and is slightly wider than the regions 11m and 11n.

Next, as shown in FIG. 11, the inner cloth 5, outer cloth 4, and reinforcing sheet 13 are heated and welded at the regions 11m and 11n.

Accordingly, the belt-shaped body 11 containing the air bladder 12 serving as the fluid bladder is formed between the inner cloth 5 and the outer cloth 4. The thickness of the belt-shaped body 11 is made substantially uniform.

Thereafter, the ring 6, which is formed integrally using a plastic material, is prepared. Then, as shown in FIG. 10, the ring attachment member 7 is folded back so as to surround the first side 61 of the ring 6, and the leading end 7e is sewn to the flat portion 7b. According to this, the ring 6 is attached to the belt-shaped body 11 via the ring attachment member 7.

Figure 12:
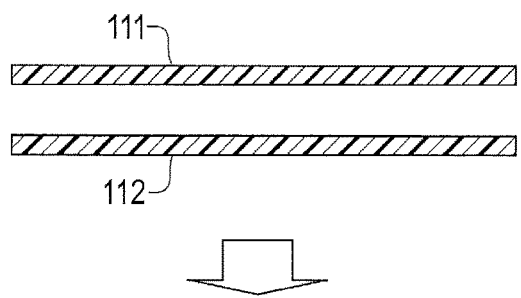
FIG. 12 is a process diagram illustrating a method of manufacturing a common belt-shaped body.
Figure 12:
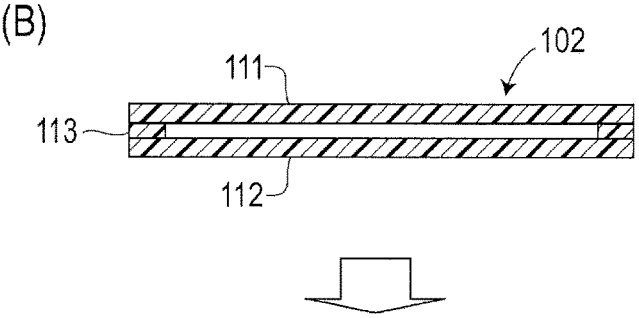
Figure 12:
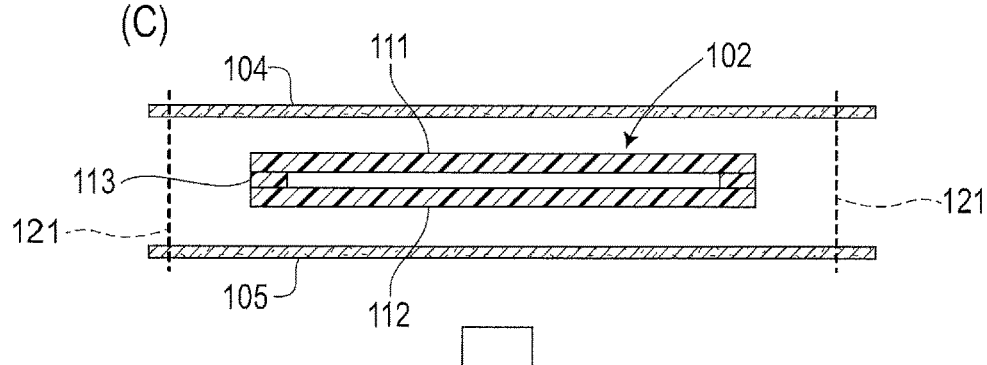
Figure 12:
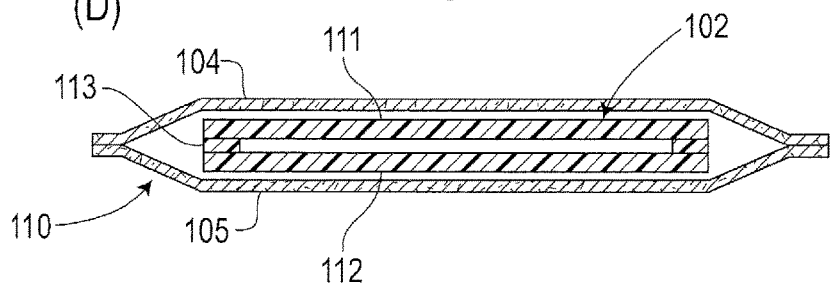
Figure 13A:
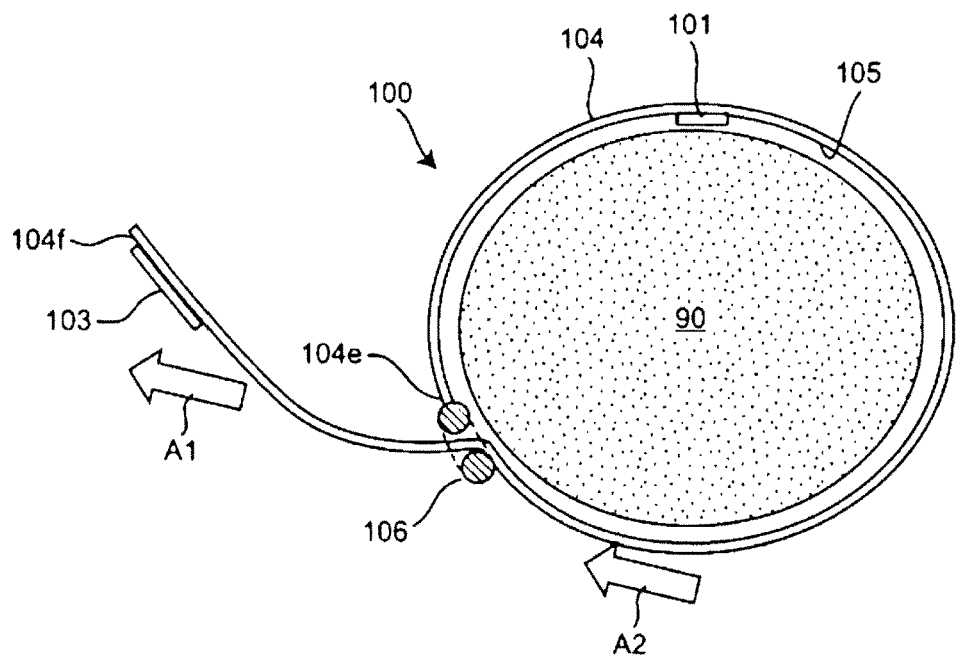
FIGS. 13(A) to 13(B) are diagrams illustrating a method of attaching a conventional cuff.
Figure 13B:
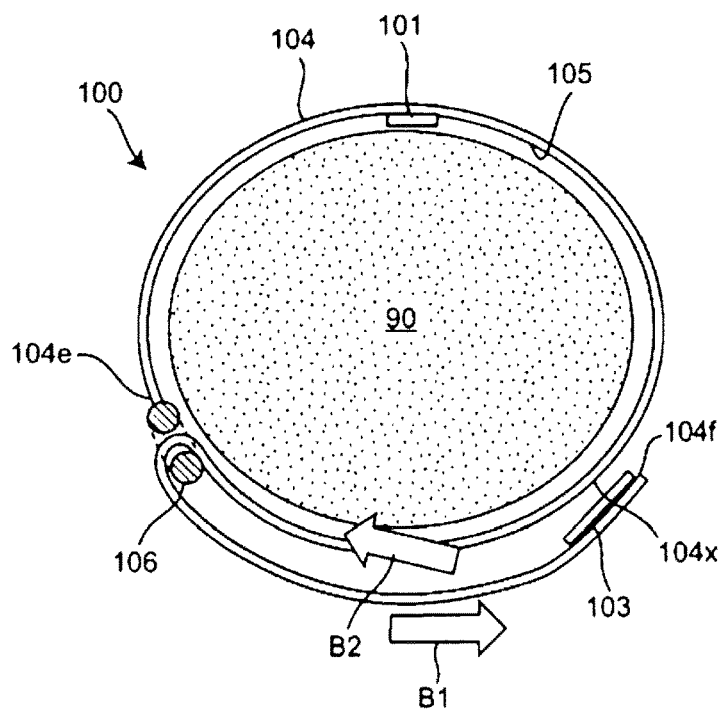

Note that FIG. 12 shows a method for manufacturing a common belt-shaped body 110.

First, as shown in FIG. 12, PVC films 111 and 112 are prepared as materials for the air bladder 102.

Next, as shown in FIG. 12, the PVC films 111 and 112 are overlaid opposite each other via the reinforcing sheet 113 composed of PVC film. Then, the PVC films 111 and 112 are welded at regions where the reinforcing sheet 113 exists. Accordingly, the air bladder 102 is formed.

Next, as shown in FIG. 12, an inner cloth 105 and an outer cloth 104 having dimensions in the circumferential direction and width direction that are greater than the dimensions of the air bladder 102 are prepared, and the inner cloth 105 and outer cloth 104 are arranged opposite each other with the air bladder 102 interposed therebetween.

Then, as shown in FIG. 12, the inner cloth 105 and outer cloth 104 are made into a bag shape by sewing peripheral edges 121 thereof together.

With the common belt-shaped body 110 formed in this way, there is a difference in the overall thickness of the cuff between the region in which the air bladder 102 exists and the regions in which it does not exist, and level differences in the external shape appear at the borders between the region in which the air bladder 102 exists and the regions in which it does not exist. For this reason, even if the ring 6 having the above-described temporary fastening structure 60 is attached, when the region continuous with the outer circumferential end of the belt-shaped body is pulled through the ring 6 during attachment, there is a possibility that a level difference will be caught in the gap 69a of the ring 6 and cannot be pulled smoothly. Note that the belt-shaped body 110 with this kind of common structure also can be used as the belt-shaped body included in the blood pressure measurement cuff of the present invention. In this case, it is desirable that the maximum thickness of the belt-shaped body 110 (thickness of the region in which the air bladder 102 exists) is approximately the same as the dimension (closest distance) d1 of the gap 69a in the ring 6.

The embodiment above is an example, and can be carried out with various modifications without departing from the scope of the invention.

REFERENCE SIGNS LIST

1 Blood pressure measurement cuff
3 Hook-and-loop fastener
4 Outer cloth
5 Inner cloth
6 Ring
7 Ring attachment member
11, 110 Belt-shaped body
60 Temporary fastening structure
65 Protrusion

The invention claimed is:

1. A blood pressure measurement cuff to be wrapped in one direction along a circumferential direction around a measurement site, the blood pressure measurement cuff comprising:

an elongated body configured to be wrapped in the circumferential direction around the measurement site, the elongated body including a fluid bladder between an inner cloth and an outer cloth, the outer cloth located on an opposite side of the fluid bladder from the inner cloth;

a ring attached via a ring attachment member to a region on an inner circumferential end side of the outer cloth; and a hook-and-loop fastener provided in a region on an outer circumferential end side of the inner cloth and configured to be detachably attached to a corresponding hook-and-loop fastener on the outer cloth;

wherein the ring comprises:

a first side and second side, each side extending in a width direction of the elongated body with the second side of the ring extending parallel to the first side;

a pair of connecting portions that connect ends of the first and second sides, with each of the pair of connecting portions extending in an elongated direction of the elongated body; and a protrusion on the first side, the protrusion configured to suppress unwrapping of the elongated body along the circumferential direction by applying a friction force to the inner cloth, the ring attachment member having a cylindrical portion that surrounds at least a portion of the first side of the ring other than the protrusion.

2. The blood pressure measurement cuff according to claim 1, wherein
the first and second sides of the ring each have plate-shaped portions, and
the pair of connecting portions of the ring have a curvature such that the plate-shaped portions of the first and second sides follow the circumferential direction around the measurement site.

3. The blood pressure measurement cuff according to claim 1, wherein
a gap between the first side and the second side of the ring is narrower at a central portion corresponding to a midpoint between the pair of connecting portions than at two remaining ends continuous with the central portion, the gap at the central portion being equal to a thickness of the region continuous with the outer circumferential end of the elongated body, and
the protrusion is composed of the central portion of the ring.

4. The blood pressure measurement cuff according to claim 3, wherein the protrusion is centrally located on the first side and protrudes in a direction towards the second side.

5. The blood pressure measurement cuff according to claim 4, wherein
the protrusion protrudes in a direction towards the second side from the measurement site, and
in a cross-sectional view along a length direction of the first or second side, an edge of the second side near the first side is formed into a circular arc shape, and
a leading end of the protrusion has an edge at a distal side with respect to the measurement site and has a rounded portion at a proximal side with respect to the measurement site.

6. The blood pressure measurement cuff according to claim 1, wherein a thickness of the elongated body is uniform.

7. The blood pressure measurement cuff according to claim 1, wherein
the hook-and-loop fastener on the outer cloth is a loop-like fastener including a plurality of loops, and the plurality of loops are angled towards the ring.

8. The blood pressure measurement cuff according to claim 1, wherein the ring is composed of an integrally-formed plastic material.

9. The blood pressure measurement cuff according to claim 3, wherein the cylindrical portion surrounds portions of the first side of the ring other than the central portion.

10. The blood pressure measurement cuff according to claim 9, wherein the ring attachment member includes a loop-like fastener including a plurality of loops on the outer circumferential surface.

11. A blood pressure measurement cuff attachment method for attaching a blood pressure measurement cuff around a measurement site, wherein the blood pressure measurement cuff comprises:
an elongated body configured to be wrapped in the circumferential direction around the measurement site, the elongated body including a fluid bladder between an inner cloth and an outer cloth, the outer cloth located on an opposite side of the fluid bladder from the inner cloth;
a ring attached via a ring attachment member to a region on an inner circumferential end side of the outer cloth; and
a hook-and-loop fastener provided in a region on an outer circumferential end side of the inner cloth and configured to be detachably attached to a corresponding hook-and-loop fastener on the outer cloth, wherein the ring comprises:
a first side and second side, each side extending in a width direction of the elongated body with the second side of the ring extending parallel to the first side;
a pair of connecting portions that connect ends of the first and second sides, with each of the pair of connecting portions extending in an elongated direction of the elongated body; and
a protrusion on the first side, the protrusion configured to suppress unwrapping of the elongated body along the circumferential direction by applying a friction force to the inner cloth, the ring attachment member having a cylindrical portion surrounds at least a portion of the first side of the ring other than the protrusion;

the method comprising:
a first arrangement step of, with the outer cloth of the elongated body on the outer side, passing the outer circumferential end of the elongated body through the ring attached to the region on the inner circumferential side of the outer cloth so as to make the elongated body into a cylinder that is wider than the measurement site;
a second arrangement step of passing the measurement site through the cylindrical elongated body, the ring being adjusted so as to be located below the measurement site in the arrangement step;
a fastening step of pulling the outer circumferential end of the elongated body through the ring so as to eliminate a gap between the inner cloth of the elongated body and the measurement site, wherein the protrusion suppresses an unwrapping of the elongated body along the circumferential direction by applying a friction force to the inner cloth; and
a fixing step of affixing the hook-and-loop fastener of the inner cloth to a corresponding hook-and-loop fastener of the outer cloth.

12. The blood pressure measurement cuff according to claim 1, wherein an elasticity of the inner cloth is greater than an elasticity of the outer cloth.

* * * * *